(12) United States Patent
Abe et al.

(10) Patent No.: US 8,658,383 B2
(45) Date of Patent: Feb. 25, 2014

(54) SWEET TASTE RECEPTOR-EXPRESSING CONSTRUCT, CELL BODY EXPRESSING THE SAME, AND UTILIZATION THEREOF

(75) Inventors: Keiko Abe, Tokyo (JP); Takumi Misaka, Tokyo (JP); Takamasa Imada, Tokyo (JP); Satoshi Fujiwara, Kawasaki (JP)

(73) Assignees: T. Hasegawa Co., Ltd., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/512,683

(22) PCT Filed: Sep. 8, 2010

(86) PCT No.: PCT/JP2010/065366
§ 371 (c)(1),
(2), (4) Date: May 30, 2012

(87) PCT Pub. No.: WO2011/067970
PCT Pub. Date: Jun. 9, 2011

(65) Prior Publication Data
US 2012/0315652 A1 Dec. 13, 2012

(30) Foreign Application Priority Data

Dec. 2, 2009 (JP) ................. 2009-274976

(51) Int. Cl.
*C12N 15/85* (2006.01)
*G01N 33/567* (2006.01)
*C07K 14/705* (2006.01)

(52) U.S. Cl.
USPC ............ 435/7.21; 435/320.1; 435/369

(58) Field of Classification Search
None
See application file for complete search history.

(56) References Cited

U.S. PATENT DOCUMENTS

| | | | |
|---|---|---|---|
| 6,955,887 B2 | 10/2005 | Adler et al. | |
| 7,294,474 B2 | 11/2007 | Zoller et al. | |
| 7,476,399 B2 | 1/2009 | Tachdjian et al. | |
| 7,888,470 B2 | 2/2011 | Li et al. | |
| 7,906,627 B2 | 3/2011 | Li et al. | |
| 8,067,235 B2 | 11/2011 | Krohn et al. | |
| 8,067,236 B2 | 11/2011 | Krohn et al. | |
| 8,124,121 B2 | 2/2012 | Tachdjian et al. | |
| 8,124,361 B2 | 2/2012 | Slack et al. | |
| 8,404,455 B2 | 3/2013 | Li et al. | |
| 2005/0026288 A1* | 2/2005 | Harms et al. | 435/456 |
| 2005/0059004 A1* | 3/2005 | Atabekov et al. | 435/6 |
| 2005/0084506 A1 | 4/2005 | Tachdjian et al. | |
| 2005/0085625 A1 | 4/2005 | Li et al. | |
| 2007/0048753 A1* | 3/2007 | McCormack et al. | 435/6 |
| 2007/0104709 A1 | 5/2007 | Li et al. | |
| 2007/0161053 A1 | 7/2007 | Li et al. | |
| 2008/0085994 A1 | 4/2008 | Li et al. | |
| 2009/0004360 A1 | 1/2009 | Bingley et al. | |
| 2009/0004651 A1 | 1/2009 | Krohn et al. | |
| 2009/0111834 A1 | 4/2009 | Tachdjian et al. | |
| 2009/0311686 A1 | 12/2009 | Slack et al. | |
| 2010/0112688 A1 | 5/2010 | Krohn et al. | |
| 2010/0120141 A1 | 5/2010 | Krohn et al. | |
| 2010/0304402 A9 | 12/2010 | Li et al. | |
| 2011/0223618 A1 | 9/2011 | Li et al. | |
| 2011/0294981 A1 | 12/2011 | Li et al. | |
| 2012/0201763 A1 | 8/2012 | Tachdjian et al. | |
| 2012/0245213 A1 | 9/2012 | Mosinger et al. | |
| 2012/0315652 A1 | 12/2012 | Abe et al. | |
| 2013/0030059 A1 | 1/2013 | Li et al. | |
| 2013/0210046 A1 | 8/2013 | Krohn et al. | |

FOREIGN PATENT DOCUMENTS

| | | |
|---|---|---|
| EP | 1865316 | 12/2007 |
| JP | 2008/013570 | 1/2008 |
| JP | 2008-13570 A | 1/2008 |
| JP | 2009/517003 | 4/2009 |
| JP | 2009-517003 A | 4/2009 |
| WO | 2005015158 A2 | 2/2005 |
| WO | 2007/121604 A2 | 11/2007 |
| WO | 2007121604 A2 | 11/2007 |
| WO | WO 2007/121604 | 11/2007 |
| WO | 2009026389 A2 | 2/2009 |

OTHER PUBLICATIONS

Li et al., Human receptors for sweet and umami taste, Apr. 2, 2002, PNAS 99(7):4692-4696.*
Invitrogen, pcDNA™ 5/FRT Expression vector designed for use with the Flp-In™ System, Oct. 14, 2008, Invitrogen Catalog No. V6010-20, Version E.*
International Search Report, dated Dec. 7, 2010, issued in corresponding PCT/JP2010/065367.
Jiang, P. et al., "Lactisole Interacts with the Transmembrane Domains of Human T1R3 to Inhibit Sweet Taste," J. Biol. Chem., 2005, vol. 280, No. 15, pp. 15238-15246; dated Dec. 7, 2010, issued in corresponding PCT/JP2010/065367.
Imada, et al., "An attempt for construction of a stably expressing cell strain of a human sweet taste receptor," Department of Applied Biological Chemistry, Graduate School of Agricultural and Life Sciences, The University of Tokyo, Mar. 5, 2009, p. 232, 3P0525A; dated Dec. 7, 2010, issued in corresponding PCT/JP2010/065366.
Invitrogen 2004 to 2005 Nenban Catalog, 10-110 to 10-117; dated Dec. 7, 2010, issued in corresponding PCT/JP2010/065366; partial English translation provided.

(Continued)

*Primary Examiner* — John Ulm
(74) *Attorney, Agent, or Firm* — Millen, White, Zelano & Branigan, P.C.

(57) ABSTRACT

[Object] An object of the present invention is to provide a sweet taste receptor-expressing construct which can functionally stably express both of a sweet taste receptor (T1R2+ T1R3) and a G protein α subunit at a high expression efficacy, and a stable expression cell body expressing the construct.
[Solution] The sweet taste receptor-expressing construct of the present invention is such that respective genes encoding sweet taste receptor subunits T1R2 and T1R3, and a G protein α subunit are inserted into the same plasmid. The cell body of the present invention is such that the sweet taste receptor-expressing construct of the present invention is gene-introduced into a 293 cell in which an FRT (Flippase Recognition Target) sequence is incorporated into one place in a genome, to express sweet taste receptor subunits T1R2 and T1R3, and a G protein α subunit simultaneously.

17 Claims, 11 Drawing Sheets

(56) References Cited

OTHER PUBLICATIONS

International Search Report, dated Dec. 7, 2010, issued in corresponding PCT/JP2010/065366.

European Search Report from corresponding European Application No. EP10834423 dated May 31, 2013.

Makoto Ohmoto, et al. "Genetic tracing of the gustatory and trigeminal neural pathways originating from T1R3—expressing taste receptor cells and solitary chemoreceptor cells" Molecular and Cellular Neuroscience vol. 38, No. 4, [Aug. 2008], pp. 505-517.

Ayako Koizumi et al. "Taste-modifying sweet protein, neoculin, is received at human T1R3 amino terminal domain" Biochemical and Biophysical Research Communications, vol. 358, No. 2, [Jun. 2007], pp. 585-589.

"Chimeric human sweet-umami and umami-sweet taste receptors", Espacenet, Publication Date: Apr. 30, 2009; English Abstract of JP-2009 517003.

European Search Report from corresponding European Patent Application No. E10834424 dated Jul. 23, 2013.

T. Imada et al., "Amiloride reduces the sweet taste intensity by inhibiting the human sweet taste receptor" Biochemical and Biophysical Research Communications, vol. 397, No. 2 [Jun. 2010], pp. 220-225.

* cited by examiner (A)

(B)

(C)

1M

500mM

200mM

100mM

50mM

20mM

SWEET TASTE RECEPTOR-EXPRESSING CONSTRUCT, CELL BODY EXPRESSING THE SAME, AND UTILIZATION THEREOF

SEQUENCE LISTING

The instant application contains a Sequence Listing which has been submitted in ASCII format via EFS-Web and is hereby incorporated by reference in its entirety. Said ASCII copy, created on Aug. 9, 2012, is named YAMAM0193SQL.txt and is 7,210 bytes in size.

TECHNICAL FIELD

The present invention relates to a sweet taste receptor-expressing construct, a cell body expressing the same, and utilization thereof, more particularly, to a sweet taste receptor-expressing construct which is useful for functionally stably expressing both of a sweet taste receptor (T1R2+T1R3) and a G protein to produce a desired sweet taste receptor-expressing cell, a cell body expressing this, and utilization thereof.

BACKGROUND ART

Taste sense is the sense generated by binding of a specific receptor present, particularly, on a surface of a tongue with a substance, when a substance is placed in a mouth. The taste sense of a mammal is constructed of five fundamental tastes, that is, a salty taste, a sour taste, a sweet taste, an umami taste and a bitter taste, and is considered to be formed by integration of these fundamental tastes. Currently, it is said that a salty taste and a sour taste are sensed via some ion channel-type receptors expressed on a cell membrane on a proximal side of taste cells present in taste buds on a surface of a tongue and, it is considered that an ion channel-type receptor consisting of PKD2L1+PKD1L3, which are a TRP channel family, functions, particularly, regarding a sour taste.

On the other hand, regarding a sweet taste, an umami taste and a bitter taste, it is considered that those tastes are sensed by signal transduction via a G protein coupled receptor (GPCR), which is a membrane protein present in taste cells, and a G protein coupling with it. Specifically, it has been revealed that a sweet taste is received with a heterodimer of T1R2+T1R3 (sweet taste receptor), an umami taste is received with a heterodimer of T1R1+T1R3 (umami taste receptor), and a bitter taste is received with about 30 kinds of molecules named as T2R family (bitter taste receptor).

The G protein is constructed of three subunits of α, β and γ. The state where α, β and γ subunits are connected is an inactive type and, when a taste substance binds to a G protein coupled receptor, GDP (guanosine 5' diphosphate) which has been bound to an α subunit is substituted with GTP, resulting in an active type in which the G protein has been dissociated into a binding body of a GTP-α subunit and a β-γ subunit.

The construction of a transduction mechanism of taste sense information has not been completely clarified, but is generally understood as follows. That is, a popular opinion is that, first, when a taste substance is bound with a receptor of taste cells, a calcium concentration in cells is raised via an information transduction process through a second messenger (IP$_3$, DAG) and the like in cells. A calcium ion supplied into cells then releases a neurotransmitter into a synapse to generate an action potential in nerve cells and, as a result, a taste sense signal starting from the receptor is transduced from a taste nerve to a brain, and the taste sense information is discriminated and determined. Recently, a theory is also being accepted, that a calcium ion opens a novel cation channel called TRPM5, and an inflow of a monovalent cation into cells causes depolarization.

Among the above-mentioned five fundamental tastes consisting of a salty taste, a sour taste, a sweet taste, an umami taste and a bitter taste, particularly, a sweet taste is a taste which is felt very tasty when a sugar content in blood is decreased. Since a sweet taste gives an image of an energy source including a sugar to a human and, further, causes a stronger feeling of satisfaction and a stronger feeling of happiness as compared with other fundamental tastes, and is deeply involved in emotion of a human, it is a taste central to determination of preference of beverages and foods.

However, a sweet taste has a higher minimum sensitivity (threshold) as compared with other fundamental tastes, and has a property that a sweet taste is sensed with difficulty in a small amount. On the other hand, when a sweet taste is too strong, this results in inducing an unhealthy image such as high calorie and obesity. For this reason, when beverages and foods with a sweet taste imparted thereto are produced, it is important to regulate an intensity of a sweet taste so that the sweet taste can be sensed by a human and preferably accepted.

An intensity of a sweet taste which is sensed when a human puts beverage and food, or the like into a mouth, has previously been verified mainly by sensory evaluation by a human. However, since sensory evaluation integrally assesses information sensed from the taste sense and the smell sense, it is difficult to verify to what extent a substance acts on the taste sense. Particularly, regarding a substance having a sweet taste not higher than a threshold, since a human cannot sense a sweet taste at a level not higher than a threshold, it is very difficult to verify an extent of a sweet taste. Further, it is very difficult to objectively assess a difference of a sweet taste sensitivity between substances. In the sensory evaluation or sensory test, a variation of evaluation between well trained assessors (called panel or panelist) cannot be neglected.

Then, it is also considered to isolate taste cells present in taste buds on a surface of a tongue, and using these isolated taste cells to assess a sweet taste intensity in place of sensory evaluation by a human. However, since taste cells isolated from those present in taste buds on a surface of a tongue are very weak in adhesion onto a culturing plate, and immediately die, they cannot be used in time-consuming assessment.

Since a sweet taste is a taste central to determination of preference of beverage and foods as described above, for example, if a substance acting on a sweet taste receptor to enhance a sweet taste can be identified, the advantageous effects such as improvement in a taste of beverage, foods and medicaments, reduction in a use amount of a sweetener, and reduction in ingested calorie can be attained. Therefore, great interest is given to such a sweet taste enhancing substance from the industrial world of beverages, foods, flavors and the like.

Then, as a new method of assessing a sweet taste intensity in place of sensory evaluation, there has been reported a method of objectively measuring and assessing a sweet taste intensity of a substance using a cell line actually expressing a sweet taste receptor.

Specifically, for example, in Example 11 of Patent Literature 1, there has been reported a cell strain generated by coexpression of hT1R2/hT1R3 by transfecting a linearized pEAK10-derived (Edge Biosystems) vector comprising an expression construct of hT1R2 (plasmid SAV2486), and a pCDNA3.1/ZEO-derived (Invitrogen) vector comprising an expression construct (plasmid SXV550) of hT1R3 into a Gα15-expressing cell strain (HEK-293 cell strain of Aurora Bioscience).

In Example 6 of Patent Literature 2, there has been disclosed a signaling system obtained by introducing a vector comprising a cDNA of hT1R2, a vector comprising a cDNA of hT1R3, a vector comprising a gene encoding a chimeric Gα protein, and a marker of a transfection efficiency pDsRed2-N1 (Takara Bio Inc.) into HEK-293T cells so that a DNA introduction ratio became a weight ratio (4:4:1:0.2) and an introduction amount became 4.6 to 5.5 µg, using a Lipofectamine 2000 reagent (Invitrogen), to coexpress hT1R2-hT1R3, and a chimeric Gα protein in HEK-293T cells.

In Example 7 of Patent Literature 3, there has been described a cell strain produced by transfecting a linear pIRES2-Puro vector (Clonetech) comprising a cDNA encoding hT1R3 into cells expressing Gα16gust44, then, transfecting a linear pcDNA4-TO vector (Invitrogen) comprising a cDNA encoding hT1R2, thereby, coexpressing hT1R2/hT1R3.

CITATION LIST

Patent Literature

Patent Literature 1: JP-A-2008-13570
Patent Literature 2: JP-A-2008-228690
Patent Literature 3: WO 2007/121604

SUMMARY OF INVENTION

Technical Problem

All of the previous cell lines expressing a sweet taste receptor are prepared by preparing or obtaining cells expressing a predetermined G protein in advance, then transfecting a vector comprising a gene encoding T1R1 and a vector comprising a gene encoding T1R3 into this, respectively.

However, when a cell line is prepared by such a method, an efficiency of introducing each vector into cells is not the same, wherein some may be preferentially introduced in some cases. Also, there are cases in which an introduced objective gene is randomly inserted into a genome of cells and, in the extreme case, an introduced objective gene is inserted into an inactive part to be not transcribed in a genome.

For this reason, the resulting cell line had the following problems.
(1) Among the previous cell lines, either one or both of T1R2 and T1R3 were not expressed and, among them, there were cell lines which were not substantially provided with a series of signal transduction mechanisms in cells. That is, it could not be said that the previous cell line is a functionally excellent model, provided with a mechanism for receiving and transducing a sweet taste.
(2) Although a G protein was expressed at an amount between cells, an expression amount and an expression ratio of T1R2 and T1R3 were different between cells, and a variation was great. For this reason, regarding assessment result with respect to a sweet taste, direct comparison between cells, particularly, direct comparison between cells which were prepared to express a G protein using a variety of point mutant constructs was difficult.
(3) With passage of cells, exclusion of introduced genes encoding T1R2 and T1R3 occurred at a high frequency and, therefore, the cell line was not a cell line which can stably express a sweet taste receptor continuously and from a view point of passage.
(4) When a G protein of a cell line is changed, it was necessary to newly prepare and obtain a cell expressing a desired G protein.
(5) It could not be necessarily said that responsiveness of cells is practically sufficient for a sweet taste substance having a high threshold, such as sucrose and the like.

Then, an object of the present invention is to provide an expression construct which can solve the above-mentioned problems, and a stable expression cell body expressing the expression construct.

Solution to Problem

In order to solve the above-mentioned problems, the present inventors continued to study and, as a result, found out that, a sweet taste receptor (T1R2+T1R3) and a G protein α subunit can be both functionally stably expressed at a high expression efficacy, by preparing an expression construct comprising an FRT site which is a specific recognition site of a Flp recombinase, and in which respective gene encoding T1R2, T1R3 and a G protein are introduced into the same plasmid, and introducing this into a predetermined cell to express T1R2, T1R3 and a G protein, resulting in completion of the present invention based on such a finding.

Thus, the present invention provides a sweet taste receptor-expressing construct in which respective genes encoding sweet taste receptor subunits T1R2 and T1R3, and a G protein α subunit are inserted into the same plasmid.

Also, the present invention provides a cell strain in which the sweet taste receptor-expressing construct according to any one of claims 1 to 12 is gene-introduced into a 293 cell in which FRT (Flippase Recognition Target) sequence has been incorporated into one place in a genome, to express sweet taste receptor subunits T1R2 and T1R3, and a G protein α subunit simultaneously.

Also, the present invention is directed to use of the cell strain for measuring a physiological response to a sweet taste substance.

Also, the present invention is directed to a method for measuring a physiological response of a sweet taste substance at a concentration of a threshold or lower of a sweet taste of the sweet taste substance, which includes adding a sweet taste enhancing substance for a particular sweet taste substance identified by measurement of a physiological response to the sweet taste substance using the cell line, upon measurement of a physiological response of the sweet taste substance.

Advantageous Effects of Invention

According to the present invention, the following effects are obtained.
(1) The sweet taste receptor-expressing construct of the present invention can functionally express T1R2, T1R3 and a G protein coupling with them, so as to generate intracellular signal transduction from stimulation of a sweet taste receptor. Therefore, a cell strain expressing the construct becomes an optimal model by which perception of a sweet taste generated by actual sweet taste reception can be objectively assessed in vivo, and can be used as a taste sense sensor for identifying or selecting a sweet taste substance, or a sweet taste regulating substance. This is extremely useful, particularly, in a high throughput screening assay. In addition, the sweet taste regulating substance means a substance which alters a physiological response from a sweet taste receptor obtained by a sweet taste substance alone, that is, an intensity of a sweet taste, by acting on a sweet taste receptor (T1R2+T1R3).

(2) The sweet taste receptor-expressing construct of the present invention can functionally express T1R2, T1R3 and a G protein coupling with them at an equivalent ratio. Therefore, according to the cell strain of the present invention, regarding a plurality of stable expression strains expressing a sweet taste receptor in which different point mutants are introduced, or a variety of G proteins, a comparative experiment by direct comparison can be conducted.

(3) The cell strain of the present invention can express T1R2, T1R3 and a G protein coupling with them over a long period of a time, and has high stability. Regardless of the passage number, since change in an expression amount of T1R2, T1R3 and a G protein coupling with them is small, the cell strain can be utilized by passage for a long period of time.

(4) When the cell strain of the present invention is prepared, it is not necessary to prepare and obtain a cell expressing a desired G protein in advance, as has previously been done.

(5) Since the cell strain of the present invention exhibits a high responsiveness to a sweet taste substance, even in the case of a substance having an intensity of a sweet taste not higher than a threshold, an intensity of a sweet taste can be assessed.

BRIEF DESCRIPTION OF DRAWINGS

FIG. 2(A) is a diagram showing a sweet taste receptor-expressing construct (A) of the first preferable specific aspect. FIG. 2(B) is a diagram showing a sweet taste receptor-expressing construct (A) of the second preferable specific aspect. FIG. 2(C) is a diagram showing a sweet taste receptor-expressing construct (A) of the third preferable specific aspect.

DESCRIPTION OF ASPECTS

Figure 1:
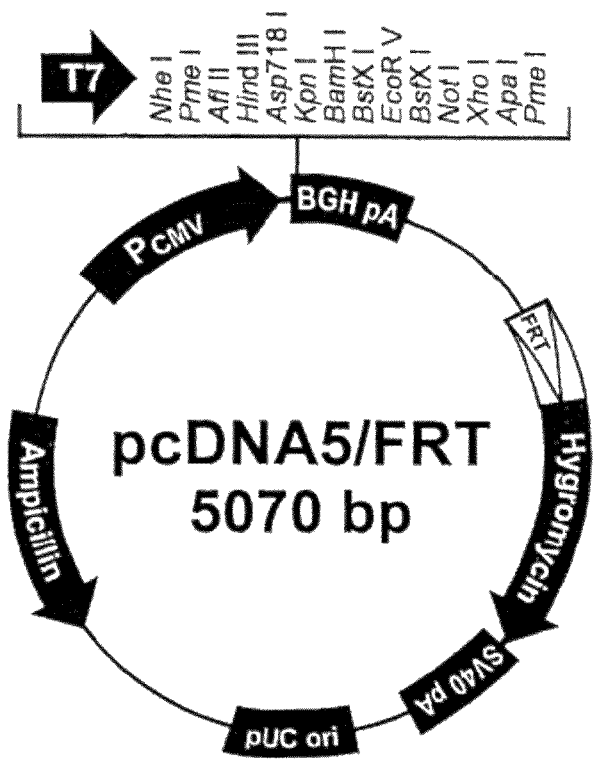
FIG. 1 is a diagram showing structure of pcDNA5/FRT (Invitrogen).

The present invention will be further explained in detail below.

In the present invention, the expression construct means a nucleic acid molecule which transfers, into cells, a DNA fragment in which a desired coding sequence, and a suitable nucleic acid sequence such as a promoter, a terminator, a marker gene, a gene encoding an FRT site, etc. required for expressing the coding sequence are connected, and has the same meaning as that of an expression vector.

There is no particular limitation on a promoter functioning as a transcription initiation signal, as long as it has the function of expressing a gene to be introduced into cells, and examples thereof include CMV (cytomegalovirus), EF-1α, SRα, CAG and the like.

Examples of the terminator which is a nucleic acid sequence for terminating transcription include SV40 pA. SV40 pA is contained on a 237 bp BamHI/BclI restriction enzyme fragment, and brings about both of termination and polyadenylation. SV40 pA derived from a bovine growth hormone (BGH) is used in many cases.

Examples of the marker gene which is a gene to be introduced as a mark for confirming that an objective gene has been introduced include a hygromycin-resistant gene, a puromycin-resistant gene, a neomycin-resistant gene, a kanamycin-resistant gene, a chloramphenicol-resistant gene and the like.

The gene encoding an FRT site corresponds to a nucleotide sequence of 2087-2047 disclosed in pFRTβGAL (STRATAGE, protocol, SEQUENCE AND SITES, Catalog #218403, May 28, 1991).

The sweet taste receptor is a heterooligomer receptor constituted by combining two subunits of T1R2 and T1R3, as described above. In the present invention, the sweet taste receptor subunits T1R2 and T1R3 include not only a human sweet taste receptor subunit (hT1R2, hT1R3), but also sweet taste receptor subunits of other animal species (mammal, fish, reptiles, amphibian, birds, etc.) such as a rat, a mouse, a pig, a dog and the like.

The sweet taste receptor subunits T1R2 and T1R3 include an entire part of each subunit, that is, all regions of seven transmembrane regions and corresponding transmembrane domains consisting of cytoplasm and extracellular loops, a venus fly trap domain, a high cysteine domain and a C-end domain.

The sweet taste receptor subunits T1R2 and T1R3 also include point mutants, and chimeras of T1R2 and T1R3.

The G protein α subunit includes G protein α subunits of various animals (mammal, fish, reptiles, amphibian, birds, etc.) such as a human, a rat, a mouse and the like, and specifically, examples include G15, hG16, or mutants in which a portion of a sequence thereof is altered (hG16gust44, hG16gust25, G15Gi3). The G protein α subunit may be appropriately determined, depending on a kind of selected sweet taste receptor subunits T1R2 and T1R3. When a human sweet taste receptor is expressed, hG16gust44 is preferable since it can be effectively responsible for information transduction between effectors in cells. In addition, hG16gust44 is a chimeric G protein in which 44 amino acid residues at a C-end part of hGα16 are replaced with Ggust.

Each cDNA encoding T1R2 and T1R3, and a G protein α subunit may be obtained by any method and, can be obtained, for example, by the known method such as a method of cloning a cDNA from an mRNA encoding the protein, chemical synthesis based on the known nucleotide sequence information, a method of isolating a genome DNA and splicing it. Nucleotide sequence information of various DNAs can be obtained by utilizing database such as NCBI. Other various genes used in the present invention are similarly obtained. In addition, cDNA means a complementary DNA, and is a reverse transcription reaction product of an mRNA transcription product.

Meanwhile, in the present invention, unless otherwise indicated, a nucleotide sequence of a nucleic acid includes, in addition to particular sequences described in the present specification, those sequences in which a substitution, deletion, insertion or addition mutant is appropriately introduced and, for example, a homologous sequence having a degenerate codon.

There is no particular limitation on the same plasmid in which the above-identified cDNAs are inserted, and specific examples thereof include pFRT/lacZeo, pUC12, pUC13, pUC19, pBR322, pBR325, pSH15, pSH19, pUB110, pC194 and the like. A plasmid which can express T1R2 and T1R3, and a G protein α subunit in a 293 cell in which an FRT site is incorporated into one place in a genome DNA is preferable in that a sweet taste receptor-expressing cell can be obtained effectively. Therefore, in the present invention, it is preferable to use commercially available pcDNA5/FRT (Invitrogen) as the same plasmid into which the above-mentioned each cDNA is inserted.

Using the Flp-In system (Invitrogen), a cultured cell strain stably expressing T1R2 and T1R3, and a G protein α subunit can be rapidly and effectively obtained. FIG. 1 shows a structure of pcDNA5/FRT (Invitrogen).

The characteristic of the sweet taste receptor-expressing construct of the present invention is in that all genes encoding sweet taste receptor subunits T1R2, T1R3 and a G protein α subunit are inserted into the same plasmid. As described above, all of the previous cell lines expressing a sweet taste receptor was prepared by preparing or obtaining a cell expressing a predetermined G protein in advance, and then individually transfecting a vector comprising a gene encoding T1R2, and a vector comprising a gene encoding T1R3, respectively, into cells, separately. As a result, there was a problem that an expression amount and an expression ratio of T1R2 and T1R3 are greatly different between cell strains.

To the contrary, the sweet taste receptor-expressing construct of the present invention can express respective genes encoding sweet taste receptor subunits T1R2 and T1R3, and a G protein α subunit rapidly and simultaneously, by having the above-mentioned characteristic. Since these three genes, after transcribed into one or two mRANs, are translated into three proteins, that is, T1R2 and T1R3, and a G protein α subunit, and express respective genes simultaneously, the above-mentioned problem does not arise.

The sweet taste receptor-expressing construct of the present invention is preferably such that respective genes encoding sweet taste receptor subunits T1R2 and T1R3, and a G protein α subunit are inserted into the same plasmid so that transcription directions are identically oriented, in order to enhance an expression efficacy of T1R2 and T1R3, and a G protein α subunit.

The sweet taste receptor-expressing construct of the present invention includes a construct comprising a gene fragment in which respective genes encoding all or two of sweet taste receptor subunits T1R2 and T1R3, and a G protein α subunit are connected via an IRES sequence, and in which the respective genes are inserted into the same plasmid so that transcription directions are identically oriented.

Also, the sweet taste receptor-expressing construct of the present invention includes a construct in which a gene encoding a G protein α subunit is connected immediately after a gene encoding a sweet taste receptor subunit T1R2 via an IRES sequence and, further, a gene encoding a G protein α subunit is connected immediately after a gene encoding a sweet taste receptor subunit T1R3 present downstream therefrom, via an IRES sequence. It is preferable that the respective genes are oriented so that transcription directions are identically oriented.

The sweet taste receptor-expressing construct of the present invention includes a construct in which a gene encoding a sweet taste receptor subunit T1R3 is connected downstream of a gene encoding a sweet taste receptor subunit T1R2 and, immediately thereafter, a gene encoding a G protein α subunit is further connected via an IRES sequence. It is preferable that the respective genes are oriented so that transcription directions are identically oriented.

The sweet taste receptor-expressing construct of the present invention includes a construct in which a gene encoding a sweet taste receptor subunit T1R2 is connected immediately after a gene encoding a sweet taste receptor subunit T1R3 via an IRES sequence and, immediately thereafter, a gene encoding a G protein α subunit is further connected via an IRES sequence. It is preferable that the respective genes are oriented so that transcription directions are identically oriented.

In the sweet taste receptor-expressing construct of the present invention, a first preferable specific aspect includes an expression construct having a sequence in which a cDNA encoding hT1R2 and a cDNA encoding hG16gust44 are connected downstream of an EF-1α promoter, so that an IRES sequence is flanked by those cDNAs, and having a sequence in which a cDNA encoding hT1R3 and a cDNA encoding hG16gust44 are connected downstream of a CMV promoter present downstream of that sequence, so that an IRES sequence is flanked by those cDNAs. It is preferable that the respective genes are oriented so that transcription directions are identically oriented. A part of a structure thereof is shown in FIG. 2(A).

In the sweet taste receptor-expressing construct of the present invention, a second preferable specific aspect includes a sweet taste receptor-expressing construct having a sequence of a cDNA encoding hT1R2 downstream of an EF-1α promoter, and having a sequence in which a cDNA encoding hT1R3 and a cDNA encoding hG16gust44 are connected downstream of a CMV promoter present downstream of that sequence, so that an IRES sequence is flanked by those cDNAs. It is preferable that the respective genes are oriented so that transcription directions are identically oriented. A part of a structure thereof is shown in FIG. 2(B).

In the sweet taste receptor-expressing construct of the present invention, a third preferable specific aspect includes a sweet taste receptor-expressing construct in which a cDNA encoding hT1R3 and a cDNA encoding hT1R2 are connected downstream of a CMV promoter, so that an IRES sequence is flanked by those cDNAs, and having a sequence in which the cDNA encoding hT1R2 and a cDNA encoding hG16gust44 are connected, so that an IRES sequence is flanked by those cDNAs. It is preferable that the respective genes are oriented so that transcription directions are identically oriented. A part of a structure thereof is shown in FIG. 2(C).

Figure 2:
FIG. 2 is a diagram showing a part of a structure of a sweet taste receptor-expressing construct of the present invention.
Figure 2:
Figure 2:

The sweet taste receptor-expressing construct of the above-mentioned first preferable specific aspect (see FIG. 2(A)) can be prepared, for example, according to the following steps (a) to (g).

Figure 3:
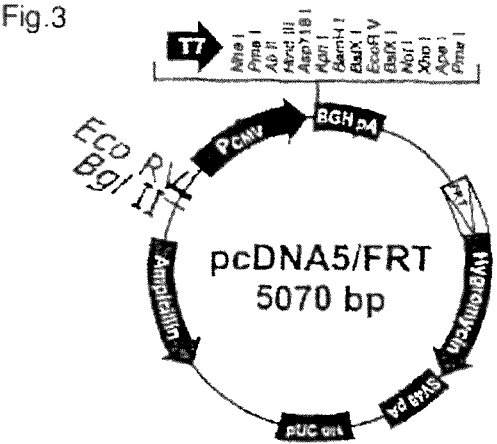
FIG. 3 is a diagram showing a product obtained in the step (a) of preparing a sweet taste receptor-expressing construct (A).

(a) Substitution of 6 bases is performed at places other than a multicloning site (base number 895 to 1010) of pcDNA5/FRT (Invitrogen), and a recognition sequence (5'-GATATC-3') of a restriction enzyme EcoRV is newly prepared (see FIG. 3).

As one preferable aspect of this step (a), an aspect of introducing a recognition sequence of EcoRV into immediately under (base number 18 to 23) a recognition sequence (base number 12 to 17) of a restriction enzyme Bgl II of pcDNA5/FRT (Invitrogen) is exemplified. This aspect can be performed, for example, according to the following substeps (a1) to (a5).

(a1) A sense primer having a recognition sequence (5'-AGATCT-3') of Bgl II at a 5'end, and a recognition sequence of EcoRV immediately under therefrom is designed and prepared. On the other hand, an antisense primer having a sequence in a BGH pA sequence is designed and prepared.

(a2) Using the sense primer and the antisense primer prepared in (a1) and, employing pcDNA5/FRT (Invitrogen) as a template, a polymerase chain reaction (PCR) is performed to amplify a DNA fragment in which respective recognition sequences of Bgl II and EcoRV are connected. In addition, PCR is the technique for amplifying a DNA sequence between a sense primer and an antisense primer, and amplification refers to increase in the copy number of a gene sequence.

PCR may be appropriately performed under the optimized condition, and specific examples include conditions of 30 seconds at 98° C.×1 cycle, (30 seconds at 98° C., 30 seconds at 55° C., 55 seconds at 72° C.)×30 cycles, 10 minutes at 72° C.×1 cycle and, then cooling to 4° C.

(a3) The DNA fragment amplified in (a2) is digested with Bgl II and Not I.

(a4) pcDNA5/FRT (Invitrogen) is digested with Bgl II and Not I.

(a5) The DNA fragment obtained in (a3) and pcDNA5/FRT (Invitrogen) obtained in (a4) are connected by a ligation reaction to prepare a vector having a recognition sequence of EcoRV immediately under a recognition sequence of Bgl II of pcDNA5/FRT (Invitrogen). The ligation reaction may be performed using a usual T4 DNA ligase, but in order to perform treatment rapidly and simply, it is preferable to use Ligation high Ver.2 (TOYOBO) which is one-liquid type DNA ligation reagent.

Figure 4:
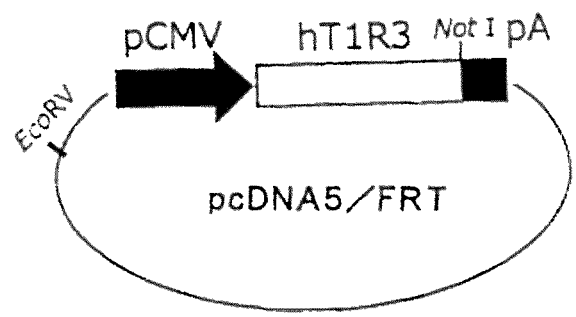
FIG. 4 is a diagram showing a product obtained in the step (b) of preparing a sweet taste receptor-expressing construct (A).

(b) A cDNA encoding hT1R3 is inserted into a multicloning site (base number 895-1010) of the vector prepared in the step (a) (see FIG. 4).

This step (b) can be implemented, for example, according to the following substeps (b1) to (b8).

(b1) A sense primer and an antisense primer having a recognition sequence (5'-GGCGCGCC-3') of Asc I and a recognition sequence (5'-GCGGCCGC-3') of Not I immediately before and immediately after a coding region of hT1R3, respectively, are designed and prepared.

(b2) Using the sense primer and the antisense primer prepared in (b1), and employing a sequence comprising a cDNA sequence encoding hT1R3 as a template, PCR is performed to amplify a cDNA encoding hT1R3.

(b3) The cDNA fragment encoding hT1R3 obtained in (b2) is digested with restriction enzymes Asc I and Not I.

(b4) pEAK10 (Edge Biosystems) is digested with restriction enzymes Asc I and Not I.

(b5) The cDNA fragment encoding hT1R3 obtained in (b3) and pEAK10 (Edge Biosystems) obtained in (b4) are connected by a ligation reaction with Ligation high Ver.2 (TOYOBO) to insert a cDNA encoding hT1R3 into pEAK10 (Edge Biosystems).

(b6) pEAK10 (Edge Biosystems) obtained in (b5) is digested with restriction enzymes Hind III and Not I, DNA fragments are separated by agarose electrophoresis, and a cDNA fragment of hT1R3 is purified.

(b7) The vector prepared in (a5) is digested with Hind III and Not I.

(b8) The cDNA fragment encoding hT1R3 obtained in (b6) and the vector obtained in (b7) are connected by a ligation reaction with Ligation high Ver.2 (TOYOBO), thereby, a cDNA encoding hT1R3 is inserted into a multicloning site of the vector prepared in (a5).

Figure 5:
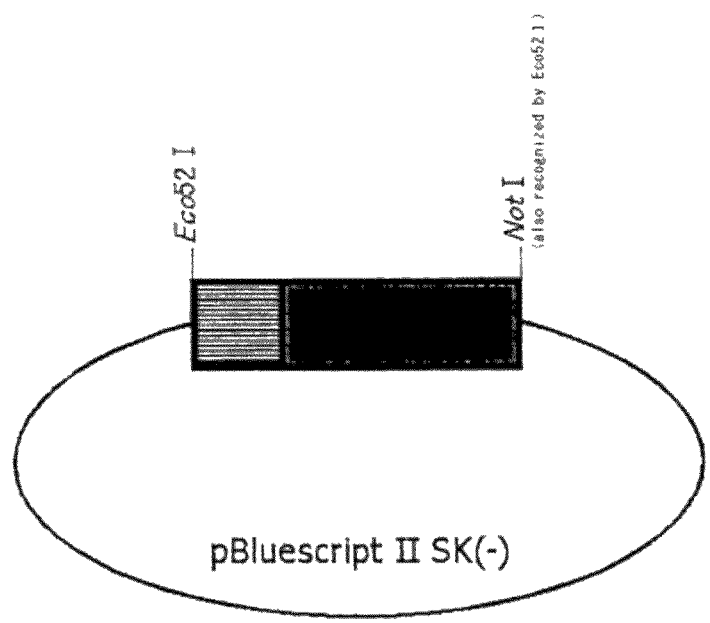
FIG. 5 is a diagram showing a product obtained in the step (c) of preparing a sweet taste receptor-expressing construct (A).

(c) Into pBluescript II SK (−) are inserted an IRES sequence, and a cDNA encoding hG16gust44, to prepare a vector (IRES2-hG16gust44/pBluescript II SK (−)) having a sequence in which these are connected (IRES2-hG16gust44 sequence) (see FIG. 5). The IRES sequence means a sequence encoding an internal ribosome entry site. This step (c) can be implemented, for example, according to the following substeps (c1) to (c11).

(c1) A sense primer having a recognition sequence (5'-CGGCCG-3') of Eco52 I immediately before an IRES sequence is designed and prepared. On the other hand, an antisense primer corresponding to a part at which an IRES sequence terminates is designed and prepared.

(c2) Using the sense primer and the antisense primer prepared in (c1), and employing pIRES2-EGFP (Clontech) as a template, PCR is performed to amplify an IRES sequence. In addition, EGFP is an abbreviation of Enhanced Green Fluorescence Protein.

(c3) A sense primer and an antisense primer having a recognition sequence (5'-GCGGCCGC-3') of Not I immediately before and immediately after a coding region of hG16gust44 are designed and prepared, and PCR is performed employing a sequence comprising a cDNA sequence encoding hG16gust44 as a template, to amplify a cDNA encoding hG16gust44. The amplified fragment is digested with Not I.

(c4) pEAK10 (Edge Biosystems) is digested with Not I.

(c5) The cDNA fragment encoding hG16gust44 obtained in (c3), and pEAK10 (Edge Biosystems) obtained in (c4) are connected by a ligation reaction with Ligation high Ver.2 (TOYOBO), to prepare a vector (hG16gust44/pEAK10) in which a cDNA encoding hG16gust44 is inserted into pEAK10 (Edge Biosystems).

(c6) A sense primer of 18 bases comprising an initiation codon of hG16gust44 is designed and prepared. On the other hand, an antisense primer having a sequence in an hGH pA sequence is designed and prepared. In addition, a pA sequence (polyadenylation sequence) is a DNA sequence which instructs termination and polyadenylation of an RNA transcription product in order to stabilize a recombinant transcription product. In addition to the pA sequence, a variety of termination sequences are known, and can be used in the sweet taste receptor-expressing construct of the present invention. The pA sequence may be an endogenous pA sequence present in a plasmid. The pA sequence which is usually used is a poly A sequence of SV40, and this poly A sequence is contained in a 237 bp restriction enzyme BamHI/BcII fragment. The pA sequence which is usually used is derived from a bovine growth hormone (BGH: Bovine Growth Hormone) gene.

(c7) Employing hG16gust44/pEAK10 obtained in (c5) as a template, and using the sense primer and the antisense primer prepared in (c6), PCR is performed to amplify a cDNA encoding hG16gust44.

(c8) The IRES sequence obtained in (c2) is digested with Eco52 I.

(c9) The cDNA encoding hG16gust44 obtained in (c7) is digested with Not I.

(c10) pBluescript II SK (−) is digested with Not I.

(c11) The IRES sequence obtained in (c8), the cDNA fragment encoding hG16gust44 obtained in (c9), and pBluescript II SK (−) obtained in (c10) are connected by a ligation reaction with Ligation high Ver.2 (TOYOBO), to prepare IRES2-hG16gust44/pBluescript II SK (−).

Figure 6:
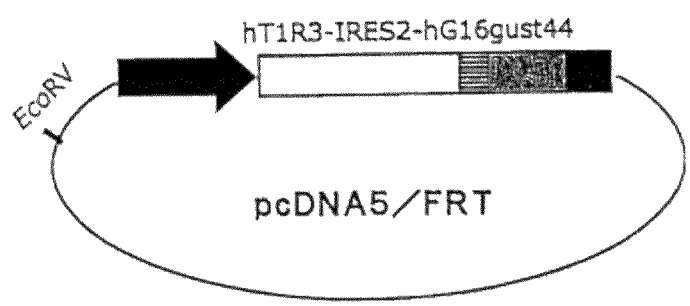
FIG. 6 is a diagram showing a product obtained in the step (d) of preparing a sweet taste receptor-expressing construct (A).

(d) A sequence (IRES2-hG16gust44 sequence) in which an IRES sequence and a cDNA encoding hG16gust44 are connected, is inserted immediately after the DNA sequence encoding hT1R3 of the vector prepared in the step (b) (see FIG. 6).

This step (d) can be implemented, for example, according to the following substeps (d1) to (d3).

(d1) IRES2-hG16gust44/pBluescript II SK (−) prepared in (c11) is digested with Eco52 I, cDNA fragments are separated by agarose electrophoresis, and an IRES2-hG16gust44 sequence is purified.

(d2) A site present immediately after the DNA sequence encoding hT1R3 of the vector prepared in (b8) is digested with Not I.

(d3) The IRES2-hG16gust44 sequence obtained in (d1), and the vector obtained in (d2) are connected by a ligation reaction with Ligation high Ver.2 (TOYOBO), to insert the IRES2-hG16gust44 sequence immediately after the DNA sequence encoding hT1R3 of the vector prepared in (b8). As a result, pcDNA5/FRT comprising hT1R3-IRES2-hG16gust44 sequence is obtained.

Figure 7:
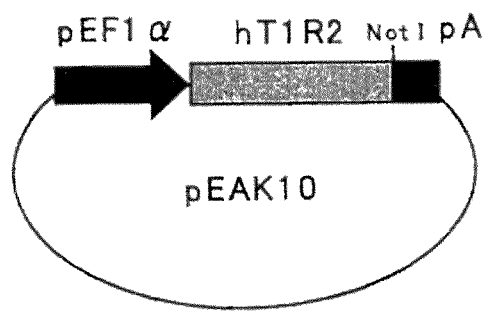
FIG. 7 is a diagram showing a product obtained in the step (e) of preparing a sweet taste receptor-expressing construct (A).

(e) A cDNA encoding hT1R2 is inserted into pEAK10 (Edge Biosystems) (see FIG. 7).

This step can be implemented, for example, according to the following substeps (e1)) to (e5).

(e1) A sense primer and an antisense primer having a recognition sequence (5'-GGCGCGCC-3') of Asc I and a recognition sequence (5'-GCGGCCGC-3') of Not I immediately before and immediately after a coding region of hT1R2, respectively, are designed and prepared.

(e2) Using the sense primer and the antisense primer prepared in (e1), and employing a sequence comprising a DNA sequence encoding hT1R2 as a template, PCR is performed to amplify a cDNA encoding hT1R2.

(e3) The cDNA encoding hT1R2 obtained in (e2) is digested with Asc I and Not I.

(e4) pEAK10 (Edge Biosystems) is digested with Asc I and Not I.

(e5) The cDNA fragment encoding hT1R2 obtained in (e3), and the pEAK10 (Edge Biosystems) obtained in (e4) are connected by a ligation reaction with Ligation high Ver.2 (TOYOBO), to insert a cDNA encoding hT1R2 into pEAK10 (Edge Biosystems).

Figure 8:
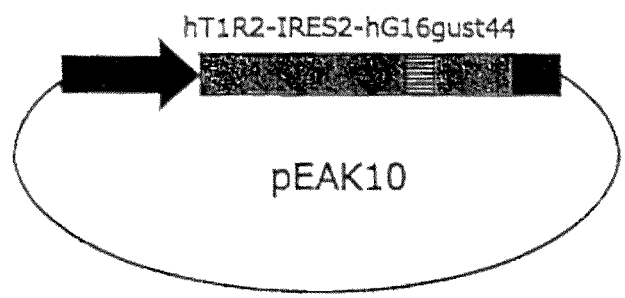
FIG. 8 is a diagram showing a product obtained in the step (f) of preparing a sweet taste receptor-expressing construct (A).

(f) An IRES2-hG16gust44 sequence is inserted immediately after the DNA sequence encoding hT1R2 of the vector prepared in the step (e) (see FIG. 8).

This step can be implemented, for example, according to the following substeps (f1) to (f3).

(f1) The IRES2-hG16gust44/pBluescript II SK (−) prepared in (c11) is digested with Eco52 I, cDNA fragments are separated by agarose electrophoresis, and an IRES2-hG16gust44 sequence is purified.

(f2) A site present immediately after the cDNA encoding hT1R2 of the vector obtained in (e5) is digested with Not I.

(f3) The IRES2-hG16gust44 sequence obtained in (f1), and the vector obtained in (f2) are connected by a ligation reaction with Ligation high Ver.2 (TOYOBO), to insert an IRES2-hG16gust44 sequence immediately after the cDNA encoding hT1R2 of the vector obtained in (e5). As a result, pEAK10 (Edge Biosystems) comprising an hT1R2-IRES2-hG16gust44 sequence is obtained.

Figure 9:
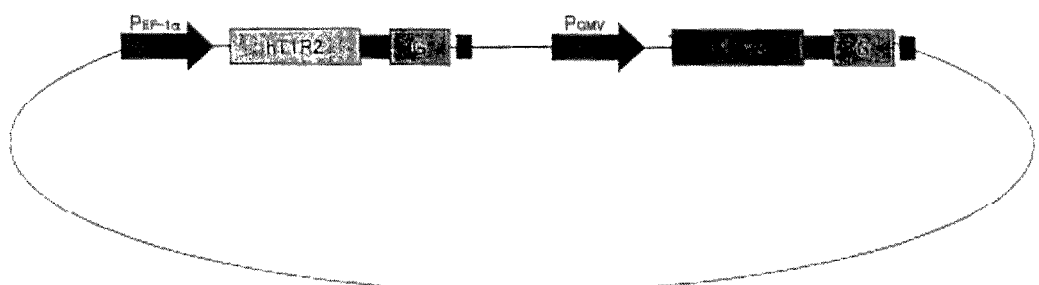
FIG. 9 is a diagram showing a product obtained in the step (g) of preparing a sweet taste receptor-expressing construct (A).

(g) The vector obtained in the step (d) is cut with EcoRV, and the hT1R2-IRES2-hG16gust44 sequence obtained in the step (f) is inserted upstream of an hT1R3-IRES2-hG16gust44 sequence, to obtain the expression construct of the above-mentioned first preferable specific aspect (see FIG. 9).

This step (g) can be implemented, for example, according to the following substeps (g1) to (g3).

(g1) A primer for performing an In-Fusion reaction is designed and prepared. Using the primer, and employing the vector prepared in (f3) as a template, a region of EF-1α promoter-hT1R2-IRES2-hG16gust44-hGH pA is amplified by PCR. The primer is designed so that about 15 bases homologous with an end of the vector obtained in (d3) which has been linearized with a restriction enzyme is added to a DNA fragment of the above-mentioned region.

(g2) The vector obtained in (d3) is digested with EcoRV.

(g3) The EF-1α promoter-hT1R2-IRES2-hG16gust44-hGH pA sequence fragment obtained in (g1), and the vector obtained in (g2) are connected using In-Fusion Advantage PCR Cloning Kit (Clontech), to prepare a sweet taste receptor-expressing construct of the first specific aspect in which the hT1R2-IRES2-hG16gust44 sequence of the vector prepared in (f3) is inserted upstream of the hT1R3-IRES2-hG16gust44 sequence of the vector obtained in (d3). In the connection with In-Fusion Advantage PCR Cloning Kit (Clontech), the EF-1 α promoter-hT1R2-IRES2-hG16gust44-hGH pA sequence fragment obtained in (g1) and the vector obtained in (g2) are mixed, an In-Fusion enzyme and a predetermined buffer are added, and a reaction is performed usually at 37° C. for 15 minutes, then, at 50° C. for 15 minutes. According to In-Fusion Advantage PCR Cloning Kit (Clontech), cloning of an objective DNA fragment is possible without undergoing limitation of a restriction enzyme site, and even in the case of a long chain DNA fragment.

Then, preparing of the sweet taste receptor-expressing construct of the above-mentioned second preferable aspect (see FIG. 2(B)) will be described.

First, the steps (a) to (e) described in preparing of the expression construct of the first preferable specific aspect are similarly performed. Thereafter, a primer for performing an In-Fusion reaction is designed and prepared. Using the primer, and employing the vector prepared in the step (e) as a template, a region of EF-1α promoter-hT1R2-hGH pA is amplified by PCR. The resulting EF-1α promoter-hT1R2-hGH pA sequence fragment, and the vector obtained in the step (d) which has been digested with EcoRV are connected using In-Fusion Advantage PCR Cloning Kit (Clontech), thereby, a sequence of EF-1α promoter-hT1R2-hGH pA, which is the PCR product, is inserted upstream of the hT1R3-IRES2-hG16gust44 sequence of the vector obtained in the step (d), to prepare a sweet taste receptor-expressing construct of the above-mentioned second preferable specific aspect.

Then, the sweet taste receptor-expressing construct of the above-mentioned third preferable specific aspect (see FIG. 2(c)) can be prepared, for example, according to the following steps (a') to (g').

(a') A cDNA encoding hT1R3 is inserted into a multicloning site (base number 895-1010) of pcDNA5/FRT (Invitrogen).

This step (a') can be implemented, for example, according to the following substeps (a'1) to (a'8).

(a'1) A sense primer and an antisense primer having a recognition sequence (5'-GGCGCGCC-3') of Asc I and a recognition sequence (5'-GCGGCCGC-3') of Not I immediately before and immediately after a coding region of hT1R3, respectively, are designed and prepared.

(a'2) Using the sense primer and the antisense primer prepared in (a'1), and employing a sequence comprising a cDNA sequence encoding hT1R3 as a template, PCR is performed to amplify a cDNA encoding hT1R3.

(a'3) The cDNA fragment encoding hT1R3 obtained in (a'2) is digested with restriction enzymes Asc I and Not I.

(a'4) And, pEAK10 (Edge Biosystems) is digested with restriction enzymes Asc I and Not I.

(a'5) The cDNA fragment encoding hT1R3 obtained in (a'3), and the pEAK10 (Edge Biosystems) obtained in (a'4) are connected by a ligation reaction with Ligation high Ver.2 (TOYOBO), to insert a cDNA encoding hT1R3 into pEAK10 (Edge Biosystems).

(a'6) The pEAK10 (Edge Biosystems) obtained in (a'5) is digested with restriction enzymes Hind III and Not I, DNA fragments are separated by agarose electrophoresis, and a cDNA fragment of hT1R3 is purified.

(a'7) pcDNA5/FRT (Invitrogen) is digested with Hind III and Not I.

(a'8) The cDNA fragment encoding hT1R3 obtained in (a'6), and the vector obtained in (a'7) are connected by a ligation reaction with Ligation high Ver.2 (TOYOBO), thereby, a cDNA encoding hT1R3 is inserted into a multicloning site of pcDNA5/FRT (Invitrogen).

(b') An IRES sequence, and a cDNA encoding hT1R2 are inserted into pBluescript II SK (−), to prepare a vector (IRES2-hT1R2/Bluescript II SK (−)) having a sequence (IRES2-hT1R2 sequence) in which these are connected.

This step (b') can be implemented, for example, according to the following substeps (b'1) to (b'16).

(b'1) A sense primer having a recognition sequence (5'-CGGCCG-3') of Eco52 I immediately before an IRES sequence is designed and prepared. On the other hand, an antisense primer corresponding to a part at which an IRES sequence terminates is designed and prepared.

(b'2) Using the sense primer and the antisense primer prepared in (b'1), and employing pIRES2-EGFP (Clontech) as a template, PCR is performed to amplify an IRES sequence.

(b'3) A sense primer and an antisense primer having a recognition sequence (5'-GGCGCGCC-3') of Asc I and a recognition sequence (5'-GCGGCCGC-3') of Not I immediately before and immediately after a coding region of hT1R2, respectively, are designed and prepared.

(b'4) Using these sense primer and antisense primer, and employing a sequence comprising a DNA sequence encoding hT1R2 as a template, PCR is performed to amplify a cDNA encoding hT1R2.

(b'5) The cDNA encoding hT1R2 obtained in (b'4) is digested with Asc I and Not I.

(b'6) pEAK10 (Edge Biosystems) is digested with Asc I and Not I.

(b'7) The cDNA fragment encoding hT1R2 obtained in (b'5), and pEAK10 (Edge Biosystems) obtained in (b'6) are connected by a ligation reaction with Ligation high Ver.2 (TOYOBO), to insert a cDNA encoding hT1R2 into pEAK10 (Edge Biosystems).

(b'8) A sense primer of 18 bases comprising an initiation codon of hT1R2 is designed and prepared. On the other hand, an antisense primer having a sequence in an hGH pA sequence is designed and prepared.

(b'9) Employing the hT1R2/pEAK10 obtained in (b'7) as a template, and using the sense primer and the antisense primer prepared in (b'8), PCR is performed to amplify a cDNA encoding hT1R2.

(b'10) The IRES sequence obtained in (b'2) is digested with Eco52 I.

(b'11) The cDNA encoding hT1R2 obtained in (b'9) is digested with Not I.

(b'12) pBluescript II SK (−) is digested with Not I.

(b'13) The IRES sequence obtained in (b'10), the cDNA fragment encoding hT1R2 obtained in (b'11), and the pBluescript II SK (−) obtained in (b'12) are connected by a ligation reaction with Ligation high Ver.2 (TOYOBO) to prepare IRES2-hT1R2/pBluescript II SK(−).

(c') A sequence (IRES2-hT1R2 sequence) in which an IRES sequence and a cDNA encoding hT1R2 are connected, is inserted immediately after the DNA sequence encoding hT1R3 of the vector prepared in the step (a').

This step (c') can be implemented, for example, according to the following substeps (c'1) to (c'3).

(c'1) IRES2-hT1R2/pBluescript II SK (−) prepared in (b'13) is digested with Eco52 I, cDNA fragments are separated by agarose electrophoresis, and an IRES2-hT1R2 sequence is purified.

(c'2) A site present immediately after the DNA sequence encoding hT1R3 of the vector prepared in (a'8) is digested with Not I.

(c'3) The IRES2-hT1R2 sequence obtained in (c'1), and the vector obtained in (c'2) are connected by a ligation reaction with Ligation high Ver.2 (TOYOBO), to insert an IRES2-hT1R2 sequence immediately after the DNA sequence encoding hT1R3 of the vector prepared in (a'8). As a result, pcDNA5/FRT comprising an hT1R3-IRES2-hT1R2 sequence is obtained.

(d') An IRES sequence, and a cDNA encoding hG16gust44 are inserted into pBluescript II SK (−) to prepare a vector (IRES2-hG16gust44/pBluescript II SK (−)) having a sequence (IRES2-hG16gust44 sequence) in which these are connected.

This step (d') can be implemented, for example, according to the following substeps (d'1) to (d'11).

(d'1) A sense primer having a recognition sequence (5'-CG-GCCG-3') of Eco52 I immediately before an IRES sequence is designed and prepared. On the other hand, an antisense primer corresponding to a part at which an IRES sequence terminates is designed and prepared.

(d'2) Using the sense primer and the antisense primer prepared in (d'1), and employing pIRES2-EGFP (Clontech) as a template, PCR is performed to amplify an IRES sequence.

(d'3) A sense primer and an antisense primer having a recognition sequence (5'-GCGGCCGC-3') of Not I immediately before and immediately after a coding region of hG16gust44 are designed and prepared. Employing a sequence comprising a cDNA sequence encoding hG16gust44 as a template, PCR is performed to amplify a cDNA encoding hG16gust44. The amplified fragment is digested with Not I.

(d'4) pEAK10 (Edge Biosystems) is digested with Not I.

(d'5) The cDNA fragment encoding hG16gust44 obtained in (d'3), and pEAK10 (Edge Biosystems) obtained in (d'4) are connected by a ligation reaction with Ligation high Ver.2 (TOYOBO), to prepare a vector (hG16gust44/pEAK10) in which a cDNA encoding hG16gust44 is inserted into pEAK10 (Edge Biosystems).

(d'6) A sense primer of 18 bases comprising an initiation codon of hG16gust44 is designed and prepared. On the other hand, an antisense primer having a sequence in an hGH pA sequence is designed and prepared.

(d'7) Employing hG16gust44/pEAK10 obtained in (d'5) as a template, and using the sense primer and the antisense primer prepared in (d'6), PCR is performed to amplify a cDNA encoding hG16gust44.

(d'8) The IRES sequence obtained in (d'2) is digested with Eco52 I.

(d'9) The cDNA encoding hG16gust44 obtained in (d'7) is digested with Not I.

(d'10) pBluescript II SK (−) is digested with Not I.

(d'11) The IRES sequence obtained in (d'8), the cDNA fragment encoding hG16gust44 obtained in (d'9), and the pBluescript II SK (−) obtained in (d'10) are connected by a ligation reaction with Ligation high Ver.2 (TOYOBO) to prepare IRES2-sG16gust44/pBluescript II SK (−).

(e') An IRES2-hG16gust44 sequence is inserted immediately after the DNA sequence encoding hT1R3-IRES2-hT1R2 of the vector prepared in the step (c').

This step can be implemented, for example, according to the following substeps (e'1) to (e'3).

(e'1) The IRES2-hG16gust44/pBluescript II SK (−) prepared in (d'11) is digested with Eco52 I, cDNA fragments are separated by agarose electrophoresis, and an IRES2-hG16gust44 sequence is purified.

(e'2) A site present immediately after the cDNA encoding hT1R2 of the vector obtained in (c'3) is digested with Not I.

(e'3) The IRES2-hG16gust44 sequence obtained in (e'1), and the vector obtained in (e'2) are connected by a ligation reaction with Ligation high Ver.2 (TOYOBO), to insert an IRES2-hG16gust44 sequence immediately after the cDNA encoding hT1R2 of the vector obtained in (c'3). Thereby, a sweet taste receptor-expressing construct of the above-mentioned third preferable specific aspect is obtained.

The resulting sweet taste receptor-expressing construct of the present invention is used for transfection into a host cell, and examples of the host cell include eukaryotic cells such as a 293 cell, a CHO cell, a 32D cell, a HeLa cell, a COS cell, a BHK cell and the like. When the cell strain of the present invention is prepared, a 293 cell in which a FRT (Flippase Recognition Target) sequence is incorporated into one place in a genome is preferable. A method of preparing this cell strain will be explained.

Preparation of the cultured cell strain is performed by cotransfection of the sweet taste receptor-expressing construct, and pOG44 being a Flp recombinase expression vector into a 293 cell in which an FRT site is incorporated into one place in a genome DNA, using the Flp-In system (Invitrogen). According to the Flp-In system (Invitrogen), an FRT site harbored in a genome DNA of a 293 cell is cleaved with a Flp recombinase which has been transiently expressed, a foreign gene is introduced into that part, and the gene is expressed. That is, respective genes encoding T1R2 and T1R3, and a G protein α subunit are introduced into an FRT site of a chromosome of a 293 cell by site-specific recombination utilizing a Flp recombinase derived from Saccharomyces cerevisiae, and an FRT site which is a target site of a Flp recombinase. As a result, a cultured cell strain stably expressing T1R2 and T1R3, and a G protein α subunit is obtained rapidly and effectively. In this cultured cell strain, respective genes encoding T1R2 and T1R3, and a G protein α subunit are transcribed with 1 or 2 mRNA(s) and, thereafter, translated into 3 proteins, that is, T1R2 and T1R3, and a G protein α subunit. As mentioned above, when the sweet taste receptor-expressing construct of the present invention is transfected into a host cell, it is preferable to use an enzyme which cuts and rebinds to a DNA site-specifically, and examples thereof include a λ integrase, a Kw recombinase and the like, in addition to a Flp recombinase.

A 293 cell in which an FRT site is incorporated into one place in a genome DNA can be prepared, for example, as follows.

First, pFRT/lacZeo being a vector for introducing an FRT site is gene-introduced into a 293 cell being a host cell, and the introduced cell is selected with Zeocin (registered trade mark). Since pFRT/lacZeo has a fusion gene of lacZ and a Zeocin-resistant gene, a cell in which pFRT/lacZeo has been introduced into a genome expresses β-galactosidase, and becomes Ziocin-regisstant. An extent of a Zeocin sensitivity can be confirmed a β-galactosidase assay.

Then, a Southern blot method for a lacZ gene is performed. Thereby, it is confirmed that an FRT site has been incorporated into only one place at a transcribable position in a genome. It is simple to use a commercially available Flp-In 293 cell (Invitrogen) as a 293 cell in which an FRT site is incorporated into one place in a genome DNA.

Preparation of the cultured cell strain of the present invention can be performed by cotransfecting the expression construct and pOG44 being an expression vector of a Flp recombinase into a 293 cell in which an FRT site has been incorporated into one place, and selecting a hygromycin B-resistant cell strain in a selection medium containing hygromycin B.

The Flp recombinase (Flippase) is one kind of enzymes which conduct a site-specific recombination reaction, and pOG44 being an expression vector of the enzyme is known. When the expression construct and pOG44 are cotransfected, since the expression construct is inserted into the FRT site of a 293 cell by the expressed Flp recombinase and a 293 cell is changed into hygromycin B-resistant and Zeocin-sensitive, whether an objective gene has been inserted or not can be easily determined, by using these drug resistances as an index.

It is possible to appropriately select, as a method of cotransfection, known methods, for example, a lipofection method, an electroporation method, a calcium phosphate-DNA precipitation method, a calcium chloride method, a calcium chloride/rubidium chloride method, a liposome method, a DEAE-dextran method, a microinjection method and the like.

Thus, a cultured cell strain in which the sweet taste receptor-expressing constructs are placed into the same position in a genome, and T1R2 and T1R3, and a G protein α subunit are simultaneously expressed can be obtained. Expression of T1R2 and T1R3, and a G protein α subunit can be confirmed by extracting proteins from the cultured cell strain, and performing a Western blot method using antibodies capable of recognizing a T1R2 antibody, a T1R3 antibody, and a G protein α subunit.

The stable expression cell is proliferated and/or maintained by culturing it in a nutrient medium. A specific method of proliferating and/or maintaining the stable expression cell may be appropriately determined, and in order to minimize desensitization with glucose, it is preferable to perform proliferation and/or maintenance at 37° C., for example, using low glucose (1,000 mg/ml) Dulbecco's modified Eagle (DMEM) medium supplemented with L-glutamine to 4 mM (Virology, Vol. 8, p. 396, 1959), to which 10% HI-FBS (Heat Inactivated Fetal Bovine Serum) and 100 µg/ml hygromycin B (Invitrogen) have been added.

Since T1R2 and T1R3, and a G protein α subunit are functionally expressed, the cultured cell strain of the present invention becomes an optimal model by which perception of a sweet taste generated by actual sweet taste reception can be objectively assessed in vivo, and can be used as a taste sense sensor for selecting a sweet taste substance. That is, for example, a sweet taste of the sweet taste substance can be assessed by using the cultured cell strain of the present invention to contact a particular sweet taste substance with the cultured cell strain, and measuring a physiological response generated by it.

A sweet taste substance being a subject for which a physiological response is measured by using the cultured cell strain of the present invention is not particularly limited, as far as it is a substance exhibiting such a sweet taste that can be sensed by a human, and examples thereof widely include saccharide-based sweeteners such as glucose, fructose, galactose, raffinose, xylose, sucrose, maltose, lactose, starch syrup, isomerized sugar, isomaltooligosaccharide, fructooligosaccharide, gal actooligosaccharide, xylooligosaccharide, lactooligosaccharide, soybean oligosaccharide, trehalose, sorbitol, mannitol, maltitol, xylitol, erythritol, lactitol, isomaltol, reduced starch syrup, reduced palatinose, Wasanbon (refined Japanese sugar), brown cane sugar, brown soft sugar, honey, molasses, licorice extract, and maple syrup, and non-saccharide-based sweeteners such as aspartame, saccharin, dulcin, stevioside, stevia extract, glycyrrhizin, Acesulfame-K, sucralose (registered trademark: San-Ei Gen F.F.I), cyclamate, alitame, neotame, perillatin, monellin, curculin (registered trademark: ADEKA) and the like.

Assessment of a sweet taste of a particular sweet taste substance using the cultured cell strain of the present invention is performed, for example, as follows.

First, as described above, a cultured cell strain expressing the sweet taste receptor-expressing construct is obtained and, then, the predetermined number of the cultured cells are seeded on each well (e.g. 10,000 to 500,000 cells/well) of a microplate having many wells (24 wells, 48 wells, 96 wells, 384 wells etc.), and cultured in a predetermined medium (e.g. DMEM medium).

Thereafter, when a particular sweet taste substance is added, a physiological response generated in the stable cultured cell strain is measured, and a sweet taste of a sweet taste substance is assessed based on the measurement results.

When a physiological response generated in the cultured cell strain is measured, phenomenon which is changed with activation of a sweet taste receptor is appropriately selected as the physiological response. When a sweet taste receptor is activated, thereafter, a variety of phenomena are initiated in cells. When a taste substance is bound to a receptor, a calcium concentration in cells is raised via an information transduction process through a second messenger ($IP_3$ (inositol triphosphate), DAG) etc. in cells. Therefore, examples of the physiological response being a measurement subject include change in a second messenger in cells and change in a calcium concentration in cells, which are changed with activation of a sweet taste receptor.

In the present invention, it is preferable that measurement of a physiological response to a sweet taste substance is performed by a calcium imaging method of observing change in a calcium concentration in cells, induced by sweet taste stimulation, from outside of cells using a fluorescent calcium indicator. Thereby, objective assessment of a sweet taste at a receptor level becomes possible, unlike the previous sensory evaluation. By digitalizing an extent of a sweet taste, intensities of a sweet taste of various substances can be compared mutually.

Since the fluorescent calcium indicator is required that fluorescent property is changed in a calcium concentration which can be physiologically changed, and change at that time is induced calcium-specifically, currently, a compound having a structure in which a complex forming site and a fluorescent chromophore are bound, is generally used as the fluorescent indicator. In the present invention, it is preferable to use Fluo-4 AM, and Fura-2 AM which are such a fluorescent calcium indicator.

When a physiological response to a sweet taste substance is measured, it is preferable that a physiological response to a sweet taste substance is digitalized and visualized by using a calcium imaging method. For example, a cell response is digitalized by a simultaneous assay with a multiplate reader and, furthermore, a change in a calcium concentration in cells is imaged by imaging using a microscope, and it is observed whether or not each cell is responding. By performing microscope observation using a fluorescent indicator different from the fluorescent indicator used in a simultaneous assay with a multiplate reader, it can be confirmed that a cell response is not due to an artifact.

The simultaneous assay with a multiplate reader may be appropriately performed according to the known method. However, it is simple and rapid to perform automated fluorescent calcium imaging using FlexStation 3 (Molecular Devices), and a high throughput assay becomes possible. FlexStation 3 is a multiplate reader in which performance of SpectraMax M5e (Molecular Devices), and a 8 channel pipetter are fused.

Automated fluorescent imaging using FlexStation 3 (Molecular Devices) can be performed, for example, according to the following procedure.

First, cells are suspended in a low glucose (1,000 mg/ml) DMEM medium from which hygromycin B has been removed, and each 70 to 80 thousands of cells are seeded on each well of a 96-well plate (Corning, CellBIND Surface).

Then, after cultured at 37° C. for 24 hours, a medium is removed and replaced with a suitable amount of a HEPES (2-[4-(2-hydroxyethyl)-1-piperazinyl]ethanesulfonic acid) buffer, and a HEPES buffer containing a fluorescent calcium indicator (Fluo-4 AM attached to Molecular Devices, FLIPR Ca 4 Assay Kit) is further added. In order to facilitate transfer into cells, a fat-soluble acetoxymethyl group has been introduced into the fluorescent indicator Fluo-4 (excitation wavelength: 495 nm, fluorescent wavelength: 518 nm), and when it is added to a medium, it is easily taken into cells, and is hydrolyzed with an esterase in cells. Hydrolyzed Fluo-4 becomes difficult to be permeated through a cell membrane, and is diffused into cells to form a complex with calcium, emitting intense fluorescence. In a 96-well plate for fluorescent observation, there are a plastic bottom and a film bottom. Since a plate of the plastic bottom is satisfactory in adherability and growth of cells, it is used at a simultaneous assay using a multiplate reader for observing an entire well. However, since a plate of this plastic bottom is bad in transmission property of a UV wavelength, and inhibits transmission of excited light of Fura-2, Fluo-4 is used.

Then, after incubated at 27 to 37° C. for 30 to 60 minutes, by adding thereto a sweet taste substance at a particular concentration or a solution of a sweet taste substance and a substance to be tested, taste stimulation is performed at 27 to 37° C.

By measuring a fluorescent reaction (excitation at 485 nm, fluorescence at 525 nm) from immediately after addition of a sweet taste substance or a sweet taste substance and a substance to be tested, to after 60 to 120 seconds, a response of a sweet taste receptor-expressing cell to sweet taste stimulation can be quantitated.

Fluorescent calcium imaging using a fluorescent microscope can be performed according to the following procedure.

First, cells are suspended in a low glucose (1,000 mg/ml) DMEM medium, from which hygromycin B has been removed, and each 40 to 80 thousands cells are seeded on each well of a 96-well plate (Greiner, Lumox).

Then, after cultured at 37° C. for 24 to 48 hours, a medium is removed and is replaced with a suitable amount of a HEPES buffer, and a HEPES buffer containing a fluorescent calcium indicator (Fura-2 AM) is further added.

After incubated at 27 to 37° C. for 30 to 60 minutes, an extracellular fluorescent indicator is removed, and this is finally replaced with a suitable amount of a HEPES buffer, and is allowed to stand at room temperature for 10 to 20 minutes. By adding thereto a sweet taste substance at a particular concentration or a solution of a sweet taste substance and a substance to be tested, taste stimulation is performed at room temperature. In the fluorescent indicator Fura-2 (excitation wavelength: 340 nm/380 nm, fluorescent wavelength: 510 nm), a fluorescent intensity of excitation at 340 nm is increased, and a fluorescent intensity of excitation at 380 nm is reduced, when a calcium ion concentration is increased.

Then, a fluorescent image (excitation at 340 nm, 380 nm, fluorescence at 510 nm) in the field of a microscope is taken in from immediately after addition of a sweet taste substance or a solution of a sweet taste substance and a substance to be tested, to after 60 to 300 seconds, and a ratio of 2-wavelength excitation fluorescence is displayed with a pseudo color, thereby, a response of a sweet taste receptor-expressing cell to sweet taste stimulation can be observed.

As described above, in the present invention, universal phenomenon not depending on an observation system can be observed upon measurement of a physiological response, by jointly using two kinds of the fluorescent indicators having different fluorescent properties in a calcium imaging method.

As described above, by using the cell strain of the present invention, a physiological response to a sweet taste substance can be measured. In addition, by adding a sweet taste enhancing substance to a particular sweet taste substance, which was identified by using measurement of a physiological response to a sweet taste substance using the cell strain of the present invention, upon measurement of a physiological response of the sweet taste substance, a physiological response can be also measured at a concentration not higher than a threshold of a sweet taste of the sweet taste substance.

EXAMPLES

The present invention will be described in more detail below by way of Examples.

Example 1

Preparation of Sweet Taste Receptor-Expressing Construct (A)

A sweet taste receptor-expressing construct (A) having a sequence in which a cDNA encoding hT1R2 and a cDNA encoding hG16gust44 are connected downstream of an EF-1α promoter, so that an IRES sequence is flanked by those cDNAs, and having a sequence in which a cDNA encoding hT1R3 and a cDNA encoding hG16gust44 are connected downstream of a CMV promoter present downstream of that sequence, so that an IRES sequence is flanked by those cDNAs (see FIG. 2(A)), was prepared according to the following procedure.

A sense primer (SEQ ID NO:1: TATAGATCTGATATC-CCCCTATGGTGCACTCTC) having a recognition sequence (5'-AGATCT-3') of Bgl II at a 5' end, and a recognition sequence of EcoRV immediately under therefrom, and an antisense primer (SEQ ID NO: 2: TAGAAGGCACAGTC-GAGG) having a sequence in a BGH pA sequence were designed and prepared.

Using these sense primer and antisense primer, and employing pcDNA5/FRT (Invitrogen) as a template, a polymerase chain reaction (PCR) was performed to amplify a DNA fragment comprising a sequence in which respective recognition sequences of Bgl II and EcoRV are connected. PCR was performed under the condition of 30 seconds at 98° C.×1 cycle, (30 seconds at 98° C., 30 seconds at 55° C., 55 seconds at 72° C.)×30 cycles, 10 minutes at 72° C.×1 cycle and, thereafter, cooling to 4° C., in all cases including Examples described later.

Then, this amplified DNA fragment was digested with Bgl II and Not I, and pcDNA5/FRT (Invitrogen) was digested with Bgl II and Not I. These restriction enzyme digestion products were connected by a ligation reaction using Ligation high Ver.2 (TOYOBO), thereby, a vector having a recognition sequence of EcoRV immediately under a recognition sequence of Bgl II of pcDNA5/FRT (Invitrogen) was prepared.

Then, a sense primer (SEQ ID NO:3: GATCGGCGCGC-CGCCATGCTGGGCCCTGCTGTC) and an antisense primer (SEQ ID NO:4: TAGAAGGCACAGTCGAGG) having a recognition sequence (5'-GGCGCGCC-3') of Asc I and a recognition sequence (5'-GCGGCCGC-3') of Not I immediately before and immediately after a coding region of hT1R3, respectively, were designed and prepared.

Using these sense primer and antisense primer, and employing a sequence comprising a cDNA sequence encoding hT1R3 as a template, PCR was performed to amplify a cDNA encoding hT1R3.

The amplified cDNA fragment encoding T1R3 was digested with Asc I and Not I, and pEAK10 (Edge Biosystems) was digested with Asc I and Not I. These restriction enzyme digestion products were connected by a ligation reaction using Ligation high Ver.2 (TOYOBO) to insert a cDNA encoding hT1R3 into pEAK10 (Edge Biosystems). Then, this was digested with Hind III and Not I, DNA fragments were separated by agarose electrophoresis, and a cDNA fragment of hT1R3 was purified.

This cDNA fragment of hT1R3, and a vector having a recognition sequence of EcoRV immediately under a recognition sequence of Bgl II of pcDNA5/FRT (Invitrogen), which had been digested with Hind III and Not I, were connected by a ligation reaction using Ligation high Ver.2 (TOYOBO), thereby, a cDNA encoding hT1R3 was inserted into a multicloning site of the vector.

Then, a sense primer (SEQ ID NO:5: GATCCGGCCGGC-CCCTCTCCCTCCCCCC) having a recognition sequence (5'-CGGCCG-3') of Eco52 I immediately before an IRES sequence and an antisense primer (SEQ ID NO:6: GGT-TGTGGCCATATTATC) corresponding to a part at which an IRES sequence terminates were designed and prepared.

Using these sense primer and antisense primer, and employing pIRES2-EGFP (Clontech) as a template, PCR was performed to amplify an IRES sequence.

A sense primer (SEQ ID NO: 7: GATCGCGGCCGCATG-GCCCGCTCGCTGACC) and an antisense primer (SEQ ID NO: 8: GATCGCGGCCGCGAATTCACTAGTGATTTA) having a recognition sequence (5'-GCGGCCGC-3') of Not I immediately before and immediately after a coding region of hG16gust44 were designed and prepared. Employing a sequence comprising a cDNA sequence encoding hG16gust44 as a template, PCR was performed to amplify a cDNA encoding hG16gust44. The amplified fragment was digested with Not I, pEAK10 (Edge Biosystems) was digested with Not I, and these were connected by a ligation reaction using Ligation high Ver.2 (TOYOBO) to prepare a vector (hG16gust44/pEAK10) in which a cDNA encoding hG16gust44 is inserted into pEAK10 (Edge Biosystems).

Then, a sense primer (SEQ ID NO:9: ATGGC-CCGCTCGCTGACC) of 18 bases comprising an initiation codon of hG16gust44, and an antisense primer (SEQ ID NO:10: CTGGATGCAGGCTACTCTA) having a sequence in an hGH pA sequence were designed and prepared.

Using these sense primer and antisense primer, and employing hG16gust44/pEAK10 as a template, PCR was performed to amplify a cDNA encoding hG16gust44.

Then, the IRES sequence digested with Eco52 I, the cDNA encoding hG16gust44 digested with Not I, and pBluescript II SK (−) digested with Not I were connected by a ligation reaction using Ligation high Ver.2 (TOYOBO) to prepare IRES2-hG16gust44/pBluescript II SK (−).

Then, the above-mentioned IRES2-hG16gust44/pBluescript II SK (−) was digested with Eco52 I, DNA fragments were separated by agarose electrophoresis, and an IRES2-hG16gust44 sequence was purified.

The pcDNA5/FRT (Invitrogen) in which a cDNA encoding hT1R3 had been inserted into a multicloning site was digested with Not I to cut a part present immediately after a DNA sequence encoding hT1R3 in the vector. This vector and the above-mentioned IRES2-hG16gust44 sequence were connected by a ligation reaction using Ligation high Ver.2 (TOYOBO) to obtain pcDNA5/FRT comprising an hT1R3-IRES2-hG16gust44 sequence, in which an IRES2-hG16gust44 sequence is inserted immediately after a DNA sequence encoding hT1R3.

Then, a sense primer (SEQ ID NO:11: GATCGGCGCGC-CGCCATGGGGCCCAGGGCAAAG) and an antisense primer (SEQ ID NO:12: GATCGCGGCCGCCTAGTC-CCTCCTCATGGT) having a recognition sequence (5'-GGCGCGCC-3') of Asc I and a recognition sequence (5'-GCGGCCGC-3') of Not I immediately before and immediately after a coding region of hT1R2, respectively, were designed and prepared.

Using these sense primer and antisense primer, and employing a sequence comprising a DNA sequence encoding hT1R2 as a template, PCR was performed to amplify a cDNA encoding hT1R2. The resulting cDNA encoding hT1R2 was digested with Asc I and Not I, pEAK10 (Edge Biosystems) was digested with Asc I and Not I, and these were connected by a ligation reaction using Ligation high Ver.2 (TOYOBO) to insert a cDNA encoding hT1R2 into pEAK10 (Edge Biosystems).

Then, the above-mentioned IRES2-hG16gust44/pBluescript II SK (−) was digested with Eco52 I, cDNA fragments were separated by agarose electrophoresis, and an IRES2-hG16gust44 sequence was purified.

pEAK10 (Edge Biosystems) in which a cDNA encoding hT1R1 had been inserted, was digested with Not I, to cut a part present immediately after a cDNA encoding hT1R2 in the vector. This vector and the above-mentioned IRES2-hG16gust44 sequence were connected by a ligation reaction using Ligation high Ver.2 (TOYOBO) to insert an IRES2-hG16gust 44 sequence immediately after a cDNA encoding hT1R2, to obtain pEAK10 (Edge Biosystems) comprising an hT1R2-IRES2-hG16gust44 sequence.

Then, primers for performing an In-Fusion reaction (SEQ ID NO:13: ATCGGGAGATCTGATGCATAACTAGT-GAGGCTC and SEQ ID NO:14: GCACCATAGGGGGAT-AGCGGATCCAGACATGAT) were designed and prepared. Using them, and employing the above-mentioned pEAK10 (Edge Biosystems) comprising an hT1R2-IRES2-hG16gust44 sequence as a template, a region of EF-1α promoter-hT1R2-IRES2-hG16gust44-hGH pA was amplified by PCR.

This EF-1α promoter-hT1R2-IRES2-hG16gust44-hGH pA sequence fragment, and pcDNA5/FRT comprising an hT1R3-IRES2-hG16gust44 sequence digested with EcoRV were connected by using In-Fusion Advantage PCR Cloning Kit (Clontech) to prepare a sweet taste receptor-expressing construct (A). It was confirmed by DNA sequencing that the resulting sweet taste receptor-expressing construct (A) has no error in a nucleotide sequence.

Example 2

Preparation of Sweet Taste Receptor-Expressing Construct (B)

A sweet taste receptor-expressing construct (B) having a sequence of a cDNA encoding hT1R2 downstream of an EF-1α promoter, and having a sequence in which a cDNA encoding hT1R3 and a cDNA encoding hG16gust44 are connected downstream of a CMV promoter present downstream of this sequence, so that an IRES sequence is flanked by those cDNAs (see FIG. 2(B)), was prepared according to the following procedure.

First, according to the step described in preparation of the sweet taste receptor-expressing construct (A) of Example 1, steps from preparation of a vector having a recognition sequence of EcoRV immediately under a recognition sequence of Bgl II of pcDNA5/FRT (Invitrogen) to insertion of a cDNA encoding hT1R2 into pEAK10 (Edge Biosystems) were implemented.

Thereafter, primers for performing an In-Fusion reaction (SEQ ID NO:15: ATCGGGAGATCTGATGCATAACTAGT-GAGGCTC and SEQ ID NO:16: GCACCATAGGGGGAT-AGCGGATCCAGACATGAT) were designed and prepared.

Using this, and employing pEAK10 (Edge Biosystems) in which a cDNA encoding hT1R2 was inserted, as a template, a region of EF-1α promoter-hT1R2-hGH pA was amplified by PCR. The resulting EF-1α promoter-hT1R2-hGH pA sequence fragment and pcDNA5/FRT (Invitrogen) comprising an hT1R3-IRES2-hG16gust44 sequence digested with EcoRV were connected by using In-Fusion Advantage PCR Cloning Kit (Clontech) to prepare a sweet taste receptor-expressing construct (B). It was confirmed by DNA sequencing that the resulting sweet taste receptor-expressing construct (B) has no error in a nucleotide sequence.

Example 3

Preparation of Sweet Taste Receptor-Expressing Construct (C)

A sweet taste receptor-expressing construct (C) in which a cDNA encoding hT1R3 and a cDNA encoding hT1R2 are connected downstream of a CMV promoter, so that an IRES sequence is flanked by those cDNAs, and having a sequence in which the cDNA encoding hT1R2 and a cDNA encoding hG16gust44 are connected, so that an IRES sequence is flanked by those cDNAs (see FIG. 2(C)), was prepared according to the following procedure.

A sense primer (SEQ ID NO:17: GATCGGCGCGCCGC-CATGCTGGGCCCTGCTGTC) and an antisense primer (SEQ ID NO:18: GATCGCGGCCGCTCACTCATGTTTC-CCCTG) having a recognition sequence (5'-GGCGCGCC-3') of Asc I and a recognition sequence (5'-GCGGCCGC-3') of Not I immediately before and immediately after a coding region of hT1R3, respectively, were designed and prepared.

Using these sense primer and antisense primer, and employing a sequence comprising a cDNA sequence encoding hT1R3 as a template, PCR was performed to amplify a cDNA encoding hT1R3.

Then, the resulting cDNA fragment encoding hT1R3 was digested with restriction enzymes Asc I and Not I, and pEAK10 (Edge Biosystems) was digested with restriction enzymes Asc I and Not I. These restriction enzyme digestion products were connected by a ligation reaction using Ligation high Ver.2 (TOYOBO) to obtain pEAK10 (Edge Biosystems) having a cDNA encoding hT1R3.

This pEAK10 (Edge Biosystems) was digested with restriction enzymes Hind III and Not I, DNA fragments were separated by agarose electrophoresis, and a cDNA fragment of hT1R3 was purified.

Then, this cDNA fragment encoding hT1R3, and pcDNA5/FRT (Invitrogen) digested with Hind III and Not I were connected by a ligation reaction using Ligation high Ver.2 (TOYOBO) to prepare pcDNA5/FRT (Invitorogen) having a cDNA encoding hT1R3 at a multicloning site.

Then, a sense primer (SEQ ID NO:19: GATCCGGCCG-GCCCCTCTCCCTCCCCCC) having a recognition sequence (5'-CGGCCG-3') of Eco52 I immediately before an IRES sequence, and an antisense primer (SEQ ID NO:20: GGTTGTGGCCATATTATC) corresponding to a part at which an IRES sequence terminates were designed and prepared.

Using these sense primer and antisense primer, and employing pIRES2-EGFP (Clontech) as a template, PCR was performed to amplify an IRES sequence.

Then, a sense primer (SEQ ID NO:21: GATCGGCGCGC-CGCCATGGGGCCCAGGGCAAAG) and an antisense primer (SEQ ID NO:22: GATCGCGGCCGCCTAGTC-CCTCCTCATGGT) having a recognition sequence (5'-GGCGCGCC-3') of Asc I and a recognition sequence (5'-GCGGCCGC-3') of Not I immediately before and immediately after a coding region of hT1R2, respectively, were designed and prepared.

Using these sense primer and antisense primer, and employing a sequence comprising a DNA sequence encoding hT1R2 as a template, PCR was performed to amplify a cDNA encoding hT1R2. The resulting cDNA encoding hT1R2 was digested with Asc I and Not I, pEAK10 (Edge Biosystems) was digested with Asc I and Not I, and these were connected by a ligation reaction using Ligation high Ver.2 (TOYOBO) to insert a cDNA encoding hT1R2 into pEAK10 (Edge Biosystems).

Then, a sense primer (SEQ ID NO:23: ATGGGGC-CCAGGGCAAAG) of 18 bases comprising an initiation codon of hT1R2, and an antisense primer (SEQ ID NO:24: CTGGATGCAGGCTACTCTA) having a sequence in an hGH pA sequence were designed and prepared.

Using these sense primer and antisense primer, and employing hT1R2/pEAK10 as a template, PCR was performed to amplify a cDNA encoding hT1R2.

Then, the above-mentioned IRES sequence was digested with Eco52 I, a cDNA encoding hT1R2 was digested with Not I, pBluescript II SK (−) was digested with Not I, and these restriction enzyme digestion products were connected by a ligation reaction using Ligation high Ver.2 (TOYOBO) to prepare IRES2-hT1R2/pBluescript II SK (−).

Then, IRES2-hT1R2/pBluescript II SK (−) was digested with Eco52 I, cDNA fragments were separated by agarose electrophoresis, and an IRES2-hT1R2 sequence was purified.

The IRES2-hT1R2 sequence, and pcDNA5/FRT (Invitrogen) having a cDNA encoding hT1R3, which had been digested with Not I, were connected by a ligation reaction using Ligation high Ver.2 (TOYOBO) to obtain pcDNA5/FRT comprising an hT1R3-IRES2-hT1R2 sequence.

Then, a sense primer (SEQ ID NO:25: GATCCGGCCG-GCCCCTCTCCCTCCCCCC) having a recognition sequence (5'-CGGCCG-3') of Eco52 I immediately before an IRES sequence, and an antisense primer (SEQ ID NO:26: GGTTGTGGCCATATTATC) corresponding to a part at which an IRES sequence terminates were designed and prepared. Using these sense primer and antisense primer, and employing pIRES2-EGFP (Clontech) as a template, PCR was performed to amplify an IRES sequence.

Then, a sense primer (SEQ ID NO:27: GATCGCGGCCG-CATGGCCCGCTCGCTGACC) and an antisense primer (SEQ ID NO:28: GATCGCGGCCGCGAATTCACTAGT-GATTTA) having a recognition sequence (5'-GCGGCCGC-3') of Not I immediately before and immediately after a coding region of hG16gust44, respectively, were designed and prepared. Employing a sequence comprising a cDNA sequence encoding hG16gust44 as a template, PCR was performed to amplify a cDNA encoding hG16gust44. The amplified fragment was digested with Not I, pEAK10 (Edge Biosystems) was digested with Not I, and these were connected by a ligation reaction using Ligation high Ver.2 (TOYOBO) to prepare a vector (hG16gust44/pEAK10) in which a cDNA encoding hG16gust44 is inserted into pEAK10 (Edge Biosystems).

Then, a sense primer (SEQ ID NO:29: ATGGC-CCGCTCGCTGACC) of 18 bases comprising an initiation codon of hG16gust44 and an antisense primer (SEQ ID NO:30: CTGGATGCAGGCTACTCTA) having a sequence in an hGH pA sequence were designed and prepared. Using these sense primer and antisense primer, and employing the above-mentioned hG16gust44/pEAK10 as a template, PCR was performed to amplify a cDNA encoding hG16gust44.

Then, the prepared IRES sequence was digested with Eco52 I, the cDNA encoding hG16gust44 was digested with Not I, pBluescript II SK (−) was digested with Not I, and these restriction enzyme digestion products were connected by a ligation reaction using Ligation high Ver.2 (TOYOBO) to prepare a vector (IRES2-hG16gust44/pBluescript II SK (−)) having an IRES2-hG16gust44 sequence.

Then, this IRES2-hG16gust44/pBluescript II SK (−) was digested with Eco52 I, cDNA fragments were separated by agarose electrophoresis, and an IRES2-hG16gust44 sequence was purified. A site present immediately after a cDNA encoding hT1R2 of pcDNA5/FRT comprising an hT1R3-IRES2-hT1R2 sequence was digested with Not I. This restriction enzyme digestion product and an IRES2-hG16gust44 sequence were connected by a ligation reaction using Ligation high Ver.2 (TOYOBO) to insert an IRES2-hG16gust44 sequence immediately after a cDNA encoding hT1R2 of pcDNA5/FRT comprising an hT1R3-IRES2-hT1R2 sequence, to prepare a sweet taste receptor-expressing construct (C). It was confirmed by DNA sequencing that the resulting sweet taste receptor-expressing construct (C) has no error in a nucleotide sequence.

Example 4

Preparation of Cultured Cell Strains (A) to (C) Expressing Human Sweet Taste Receptors (hT1R2+hT1R3) and hG16gust44

The sweet taste receptor-expressing construct (A) (0.8 μg) prepared in Example 1, and 7.2 μg of pOG44 were transfected into 2 million of Flp-In-293 cells (Invitrogen) by a lipofection method and, after 48 hours passed, screening was performed with a hygromycin B-added (100 μg/ml) medium to obtain a cultured cell strain (A) which is a stable expression strain.

Then, cells which survived to hygromycin B were proliferated and a part of it was cultured in a Zeocin-added (100 μg/ml) medium. Since cells died due to Zeocin (100 μg/ml), it was confirmed that genes of a human sweet taste receptor (hT1R2+hT1R3) and hG16gust44 are introduced into an FRT site, in the cultured cell strain (A).

Regarding cultured cell strains (A) to (C), RT-PCR was performed, and bands of an hT1R2 fragment, an hT1R3 fragment and an hG16gust44 fragment were recognized by agarose electrophoresis, and it was confirmed that a human sweet taste receptor (hT1R2+hT1R3) and hG16gust44 are expressed.

Similarly, using sweet receptor-expressing constructs (B) and (C) prepared in Example 2, respectively, in place of the sweet taste receptor-expressing construct (A), a cultured cell strain (B) and a cultured cell strain (C) were prepared.

Thereafter, these cultured cell strains (A) to (C) were proliferated and maintained at 37° C. in a low glucose (1,000 mg/ml) Dulbecco's modified Eagle (BMEM) medium containing 10% HI-FBS (Heat Inactivated Fetal Bovine Serum), 100 μg/ml of hygromycin B (Invitorogen), and 4 mM of L-glutamine.

Example 5

Comparison of Physiological Response of Cultured Cell Strains (A) to (C) Prepared in Example 4, to Aspartame Stimulation Each of the cultured cell strains (A) to (C) prepared in Example 4 was loaded with a fluorescent calcium indicator Fura-2 AM, and cells were prepared to take them in. Cells loaded with Fura-2 AM were excited at 340 nm and 380 nm, and a fluorescent image observed at 510 nm was taken using a fluorescent microscope and a CCD camera. While the image was taken, Aspartame at a final concentration of 10 mM was administered to cells and, thereafter, the image was continuously taken. From the field of the taken image, 100 cells were randomly selected, and the response cell number was counted.

Figure 10:
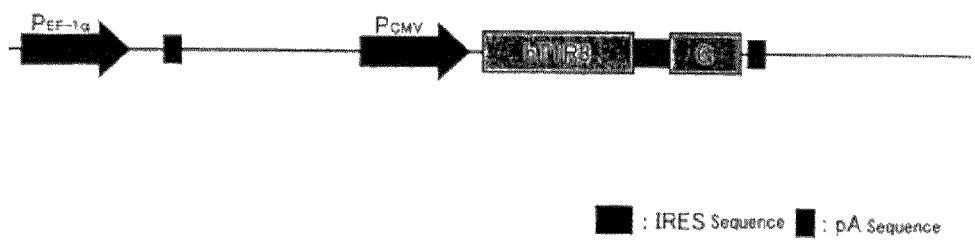
FIG. 10 is a diagram showing a part of a structure of an expressing construct used for comparison in Example 5.

As comparison, using an expression construct consisting of pcDNA5/FRT having a sequence in which a cDNA encoding hT1R3 and a cDNA encoding hG16gust44 are connected downstream of a CMV promoter, so that an IRES sequence is flanked by those cDNAs (FIG. 10), a cultured cell strain (D) was prepared similarly as in Example 4, and the response cell number was subjected to counting as described above.

Figure 11:
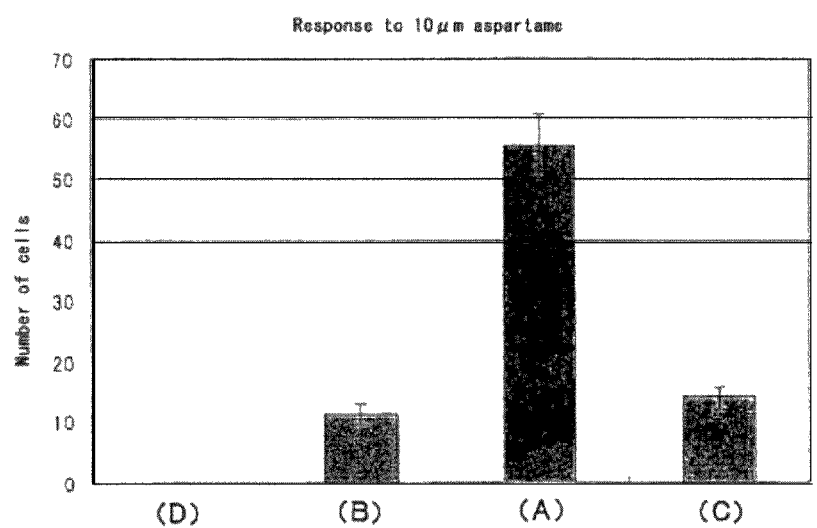
FIG. 11 is a graph showing the results of the number of cells responded to aspartame stimulation.

The result of counting is show in FIG. 11. As seen from this result, regarding the cultured cell strain (A), a very strong cell response was observed by administration of Aspartame and, regarding the cultured cell strains (B) and (C), a weaker cell response was observed as compared with the cultured cell strain (A), while in the cultured cell strain (D), a cell response was not observed. Therefore, it was confirmed that in the cultured cell strains (A) to (C), a human sweet taste receptor is functionally expressed.

Example 6

Physiological Response of Cultured Cell Strain (A) to Aspartame Stimulation

Figure 12:
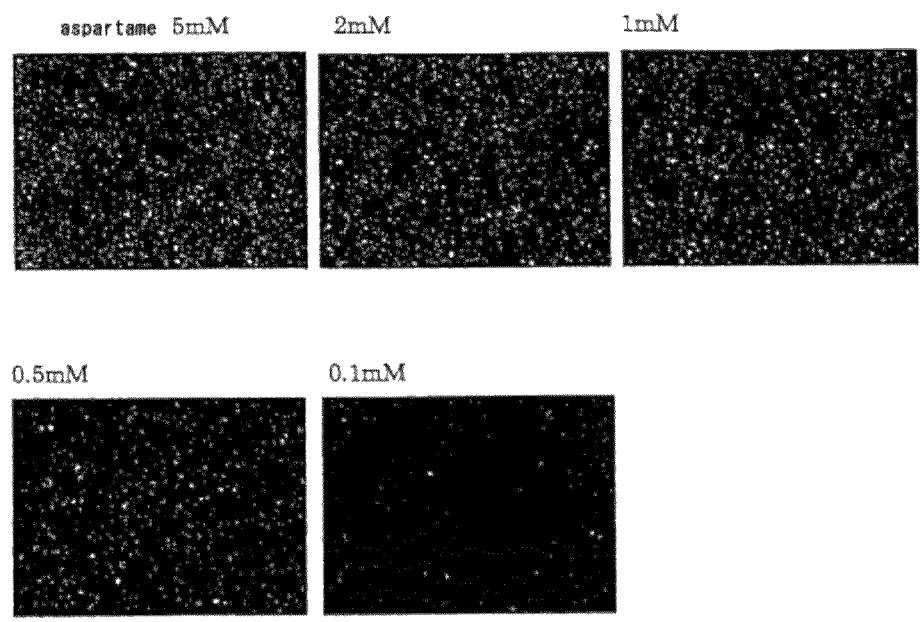
FIG. 12 is a diagram showing fluorescent images in case of administering aspartame to a cultured cell strain (A).

The cultured cell strain (A) prepared in Example 4 was loaded with a fluorescent calcium indicator (Fura-2) AM, and cells were prepared to take it in. Cells loaded with Fura-2 AM were excited at 340 nm and 380 nm, and a fluorescent image observed at 510 nm was taken using a fluorescent microscope and a CCD camera. While the image was taken, Aspartame at each final concentration of 0.1 mM, 0.5 mM, 1 mM, 2 mM and 5 mM was administered to cells and then the image was continuously taken. Images at the time point at which a strongest response was observed at each concentration are shown in FIG. 12. As seen from the result, when Aspartame is used as a sweetener to be administered, a concentration-dependent sweet taste response was observed in a range of 0.1 mM to 5 mM.

Example 7

Physiological Response of Cultured Cell Strain (A) to Sucrose Stimulation

Figure 13:
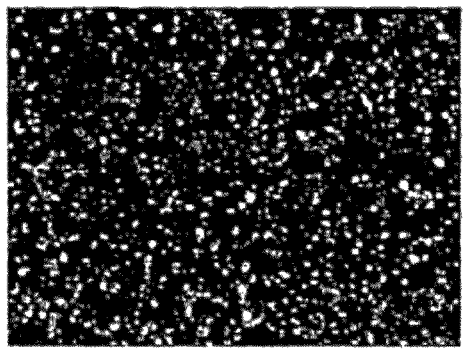
FIG. 13 is a diagram showing fluorescent images in case of administering sucrose to a cultured cell strain (A).
Figure 13:
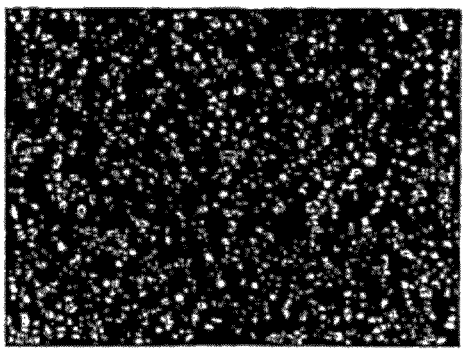
Figure 13:
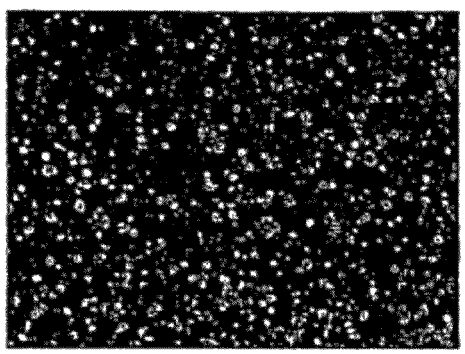
Figure 13:
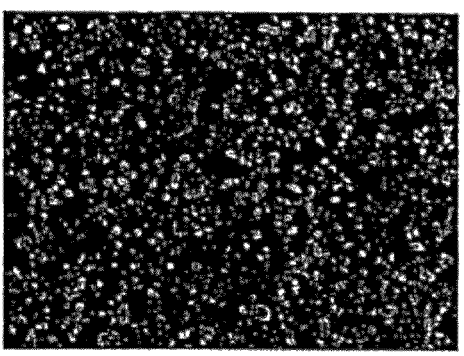
Figure 13:
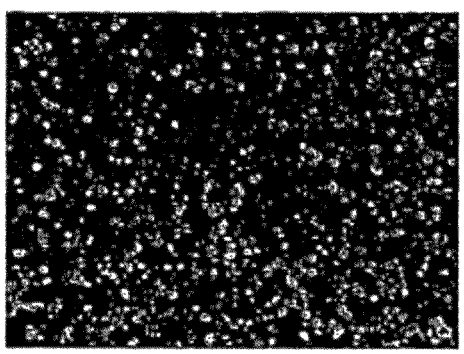
Figure 13:
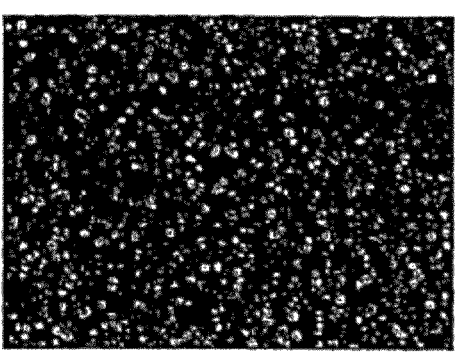

The cultured cell strain (A) prepared in Example 4 was loaded with a fluorescent calcium indicator (Fura-2) AM, and cells were prepared to take it in. Cells loaded with Fura-2 AM were excited at 340 nm and 380 nm, and a fluorescent image observed at 510 nm was taken by using a fluorescent microscope and a CCD camera. While the image was taken, Sucrose at each final concentration of 20 mM, 50 mM, 100 mM, 200 mM, 500 mM and 1 M was administered to cells and then the image was continuously taken. Images at the time point at which a strongest response was observed at each concentration are shown in FIG. 13.

As seen from the result, when Sucrose is used as a sweetener to be administered, a concentration-dependent sweet taste response was observed in a range of 20 mM to 1 M.

Example 8

Physiological Response of Cultured Cell Strain (A) to Sucrose Stimulation

Figure 14:
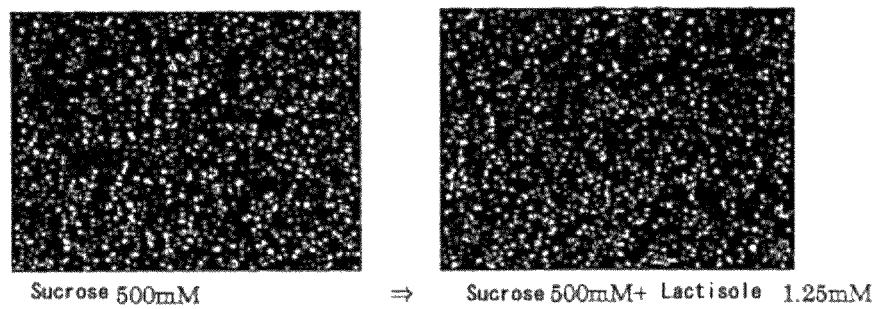
FIG. 14 is a diagram showing fluorescent images in case of administering sucrose and lactisole to a cultured cell strain (A).

The cultured cell strain (A) prepared in Example 4 was loaded with a fluorescent calcium indicator (Fura-2) AM, and cells were prepared to take it in. Cells loaded with Fura-2 AM were excited at 340 nm and 380 nm, and a fluorescent image observed at 510 nm was taken by using a fluorescent microscope and a CCD camera. While the image was taken, sucrose at final concentration of 500 mM was administered to cells and then the image was continuously taken. Images at the time point at which a strongest response was observed are shown in FIG. 14. Sucrose at final concentration of 500 mM and lactisole at final concentration of 1.25 mM were simultaneously administered to cells and then the image was continuously taken in the same way as described above. Images at the time point at which a strongest response was observed are shown in FIG. 14.

As is apparent from the above results, it could be confirmed that a response of cells were suppressed by the addition of lactisole known as a T1R3 inhibitor. It was estimated from the results that a response of cells to sucrose is a response via a T1R3 subunit.

Example 9

Physiological Response of Cultured Cell Strain (A) to Sucrose Stimulation

A physiological response of the cultured cell strain (A) to sucrose stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing sucrose, so that a final concentration of sucrose became a concentration described in Table 1, and sucrose stimulation was performed at 27° C.

Figure 15:
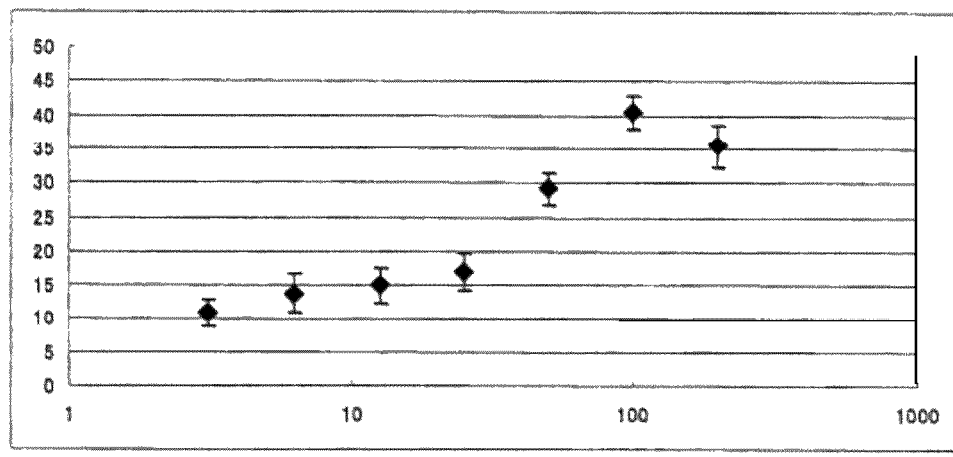
FIG. 15 shows a sucrose concentration-response curve in case of administering sucrose to a cultured cell strain (A).

A fluorescent reaction (excitation at 485 nm, fluorescence at 525 nm) from immediately after addition of a HEPES buffer containing sucrose to after 100 seconds was measured by using FlexStation 3 (Molecular Devices), and a response of a sweet taste receptor-expressing cell to sucrose stimulation was quantitated by automated fluorescent imaging. Results are shown in Table 1 and FIG. 15. The vertical axis of FIG. 15 is a maximum of change (ΔF) in a fluorescent intensity between immediately after stimulation and 100 seconds after stimulation, that is, a response intensity of cells, and the horizontal axis indicates a sucrose concentration (mM) expressed by logarithm.

From the obtained result, it could be confirmed that a sweet taste of sucrose can be assessed by using the cultured cell strain (A) of the present invention. Since sucrose is weak in an extent of a sweet taste, unless added at a concentration of around 50 mM, a response of a sweet taste receptor cell is not observed. However, conversely, when a sucrose solution at a concentration exceeding 200 mM is added, since cells undergo influence of an osmotic pressure, it becomes impossible to measure a normal cell response. Therefore, usually, being capable of digitalizing a sweet taste degree of sucrose in a sweet taste assay system using cells is limited to a narrow range of about 50 to 200 mM, but by utilizing the above-mentioned cell system, it becomes possible to further reduce a lower limit of this limitation value.

TABLE 1

| Addition concentration of Sucrose (mM) | Change amount of fluorescent intensity (ΔF) Average ± S.E., n = 6 |
|---|---|
| 0 | 10.6 ± 2.4 |
| 3.1 | 10.8 ± 2.0 |
| 6.3 | 13.8 ± 2.9 |
| 12.5 | 14.9 ± 2.7 |
| 25 | 17.0 ± 2.6 |
| 50 | 29.2 ± 2.3 |
| 100 | 40.4 ± 2.5 |
| 200 | 35.4 ± 3.2 |

Example 10

Physiological Response of Cultured Cell Strain (A) to D-Phenylalanine Stimulation A physiological response of the cultured cell strain (A) to D-phenylalanine stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing D-phenylalanine, so that a final concentration of D-phenylalanine became a concentration described in Table 2, and D-phenylalanine stimulation was performed at 27° C.

Figure 16:
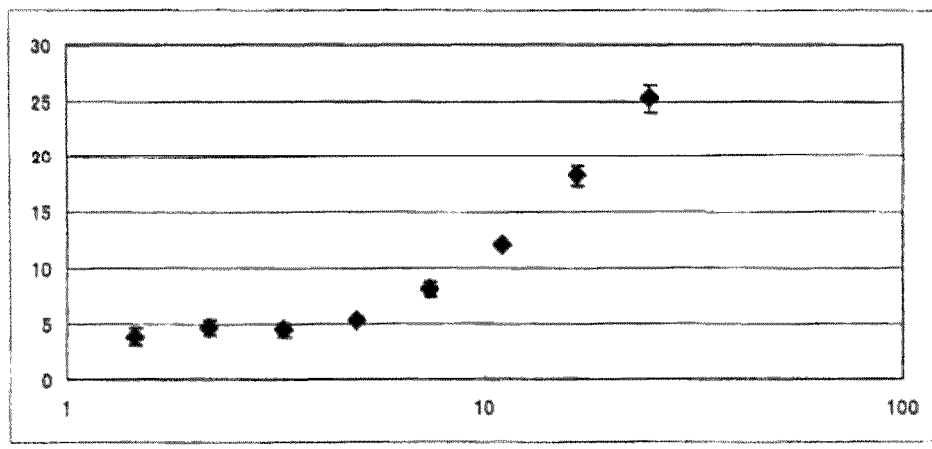
FIG. 16 shows a D-phenylalanine concentration-response curve in case of administering D-phenylalanine to a cultured cell strain (A).

A fluorescent reaction (excitation at 485 nm, fluorescence at 525 nm) from immediately after addition of a HEPES buffer containing D-phenylalanine to after 100 seconds was measured using FlexStation 3 (Molecular Devices), and a response of a sweet taste receptor-expressing cell to D-phenylalanine stimulation was quantitated by automated fluorescent imaging. Results are shown in Table 2 and FIG. 16. The vertical axis of FIG. 16 is a maximum of change (ΔF) in a fluorescent intensity between immediately after stimulation and 100 seconds after stimulation, that is, a response intensity of cells, and the horizontal axis indicates a D-phenylalanine concentration (mM) expressed by logarithm.

From the obtained result, it could be confirmed that a sweet taste of D-phenylalanine can be assessed by using the cultured cell strain (A) of the present invention.

TABLE 2

| Addition concentration of D-phenylalanine (mM) | Change amount of fluorescent intensity (ΔF) Average ± S.E., n = 2 |
| --- | --- |
| 1.5 | 4.0 ± 0.8 |
| 2.2 | 4.8 ± 0.6 |
| 3.3 | 4.5 ± 0.6 |
| 4.9 | 5.4 ± 0.3 |
| 7.4 | 8.1 ± 0.7 |
| 11.1 | 12.1 ± 0.2 |
| 16.7 | 18.2 ± 0.9 |
| 25 | 25.2 ± 1.2 |

Example 11

Physiological Response of Cultured Cell Strain (A) to Aspartame Stimulation

A physiological response of the cultured cell strain (A) to aspartame stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing aspartame, so that a final concentration of aspartame became a concentration described in Table 3, and aspartame stimulation was performed at 27° C.

Figure 17:
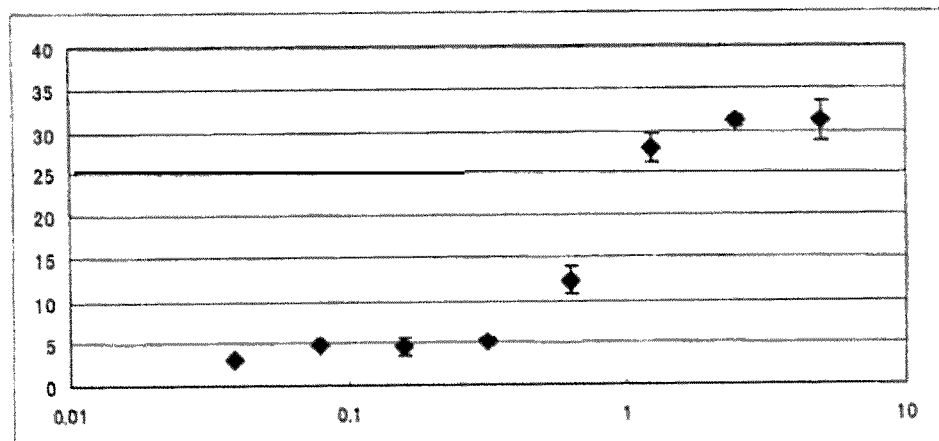
FIG. 17 shows an aspartame concentration-response curve in case of administering aspartame to a cultured cell strain (A).

A fluorescent reaction (excitation at 485 nm, fluorescence at 525 nm) from immediately after addition of a HEPES buffer containing aspartame to after 100 seconds was measured using FlexStation 3 (Molecular Devices), and a response of a sweet taste receptor-expressing cell to aspartame stimulation was quantitated by automated fluorescent imaging. Results are shown in Table 3 and FIG. 17. The vertical axis of FIG. 17 is a maximum of change (ΔF) in a fluorescent intensity between immediately after stimulation and 100 seconds after stimulation, that is, a response intensity of cells, and the horizontal axis indicates an aspartame concentration (mM) expressed by logarithm.

From the obtained result, it could be confirmed that a sweet taste of aspartame can be assessed by using the cultured cell strain (A) of the present invention.

TABLE 3

| Addition concentration of aspartame (mM) | Change amount of fluorescent intensity (ΔF) Average ± S.E., n = 2 |
| --- | --- |
| 0.04 | 3.0 ± 0.1 |
| 0.08 | 4.8 ± 0.1 |
| 0.16 | 4.4 ± 1.1 |
| 0.31 | 5.2 ± 0.4 |
| 0.63 | 12.3 ± 1.7 |
| 1.25 | 27.9 ± 1.9 |
| 2.50 | 31.2 ± 0.7 |
| 5 | 31.1 ± 2.4 |

Example 12

Physiological Response of Cultured Cell Strain (A) to Saccharin Stimulation

A physiological response of the cultured cell strain (A) to saccharin stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing saccharin, so that a final concentration of saccharin became a concentration described in Table 4, and saccharin stimulation was performed at 27° C.

Figure 18:
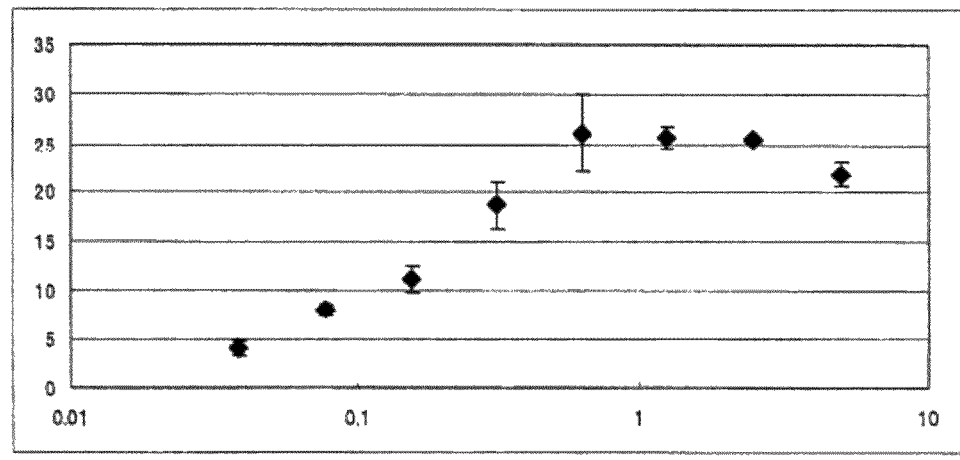
FIG. 18 shows a saccharin concentration-response curve in case of administering saccharin to a cultured cell strain (A).

A fluorescent reaction (excitation at 485 nm, fluorescence at 525 nm) from immediately after addition of a HEPES buffer containing saccharin to after 100 seconds was measured by using FlexStation 3 (Molecular Devices), and a response of a sweet taste receptor-expressing cell to saccharin stimulation was quantitated by automated fluorescent imaging. Results are shown in Table 4 and FIG. 18. The vertical axis of FIG. 18 is a maximum of change (ΔF) in a fluorescent intensity between immediately after stimulation and 100 seconds after stimulation, that is, a response intensity of cells, and the horizontal axis indicates an saccharin concentration (mM) expressed by logarithm.

From the obtained result, it could be confirmed that a sweet taste of saccharin can be assessed by using the cultured cell strain (A) of the present invention.

TABLE 4

| Addition concentration of saccharin (mM) | Change amount of fluorescent intensity (ΔF) Average ± S.E., n = 2 |
| --- | --- |
| 0.04 | 4.0 ± 0.8 |
| 0.08 | 8.0 ± 0.6 |
| 0.16 | 11.1 ± 1.3 |
| 0.31 | 18.7 ± 2.4 |
| 0.63 | 26.1 ± 4.0 |
| 1.25 | 25.7 ± 1.1 |
| 2.50 | 25.6 ± 0.2 |
| 5 | 21.8 ± 1.2 |

Example 13

Physiological Response of Cultured Cell Strain (A) to Stevia Stimulation

A physiological response of the cultured cell strain (A) to stevia stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing stevia, so that a final concentration of stevia became a concentration described in Table 5, and stevia stimulation was performed at 27° C.

Figure 19:
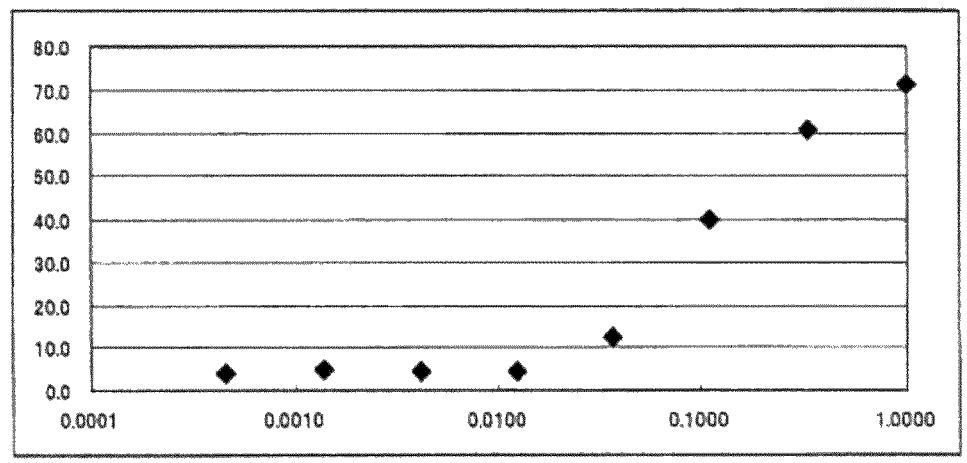
FIG. 19 shows a stevia concentration-response curve in case of administering stevia to a cultured cell strain (A).

A fluorescent reaction (excitation at 485 nm, fluorescence at 525 nm) from immediately after addition of a HEPES buffer containing stevia to after 100 seconds was measured by using FlexStation 3 (Molecular Devices), and a response of a sweet taste receptor-expressing cell to stevia stimulation was quantitated by automated fluorescent imaging. Results are shown in Table 5 and FIG. 19. The vertical axis of FIG. 19 is a maximum of change (OF) in a fluorescent intensity between immediately after stimulation and 100 seconds after stimulation, that is, a response intensity of cells, and the horizontal axis indicates a stevia concentration (mM) expressed by logarithm.

From the obtained result, it could be confirmed that a sweet taste of stevia can be assessed by using the cultured cell strain (A) of the present invention.

TABLE 5

| Addition concentration of stevia (mg/ml) | Change amount of fluorescent intensity (ΔF) |
|---|---|
| 0.0005 | 3.9 |
| 0.0014 | 4.7 |
| 0.004 | 4.2 |
| 0.01 | 4.2 |
| 0.04 | 12.2 |
| 0.11 | 39.7 |
| 0.33 | 61.0 |
| 1 | 71.4 |

Example 14

Physiological Response of Cultured Cell Strain (A) to Neohesperidin Dihydrochalcone (NHDC) Stimulation A physiological response of the cultured cell strain (A) to neohesperidin dihydrochalcone stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing neohesperidin dihydrochalcone, so that a final concentration of neohesperidin dihydrochalcone became a concentration described in Table 6, and neohesperidin dihydrochalcone stimulation was performed at 27° C.

Figure 20:
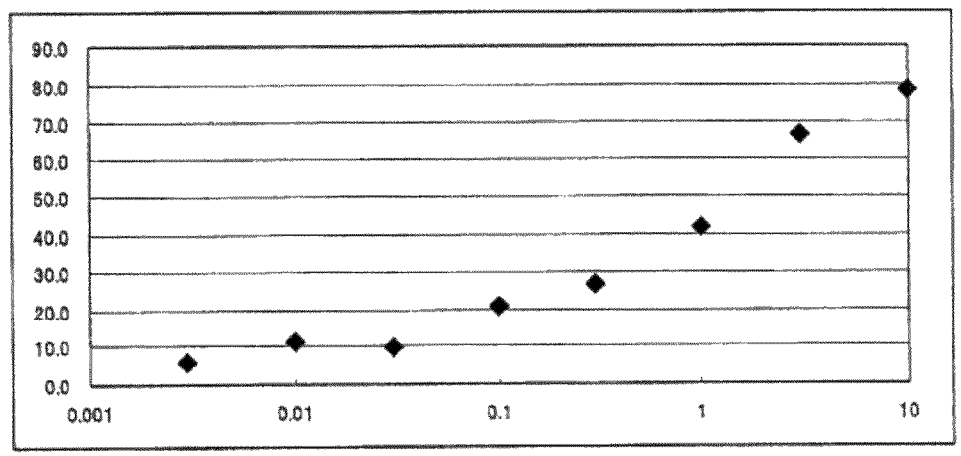
FIG. 20 shows a neohesperidin dihydrochalcone (NHDC) concentration-response curve in case of administering neohesperidin dihydrochalcone (NHDC) to a cultured cell strain (A).

A fluorescent reaction (excitation at 485 nm, fluorescence at 525 nm) from immediately after addition of a HEPES buffer containing neohesperidin dihydrochalcone to after 100 seconds was measured by using FlexStation 3 (Molecular Devices), and a response of a sweet taste receptor-expressing cell to neohesperidin dihydrochalcone stimulation was quantitated by automated fluorescent imaging. Results are shown in Table 6 and FIG. 20. The vertical axis of FIG. 20 is a maximum of change (AF) in a fluorescent intensity between immediately after stimulation and 100 seconds after stimulation, that is, a response intensity of cells, and the horizontal axis indicates a neohesperidin dihydrochalcone concentration (mM) expressed by logarithm.

From the obtained result, it could be confirmed that a sweet taste of neohesperidin dihydrochalcone can be assessed by using the cultured cell strain (A) of the present invention.

TABLE 6

| Addition concentration of NHDC (mM) | Change amount of fluorescent intensity (ΔF) |
|---|---|
| 0.003 | 5.8 |
| 0.01 | 11.2 |
| 0.03 | 9.6 |
| 0.1 | 20.9 |
| 0.3 | 26.7 |
| 1 | 41.8 |
| 3 | 66.8 |
| 10 | 78.6 |

Example 15

Physiological Response of Cultured Cell Strain (A) to Cyclamate Stimulation

A physiological response of the cultured cell strain (A) to cyclamate stimulation was analyzed by automated fluorescent imaging.

The cultured cell strain (A) prepared in Example 4 was trypsinized, and suspended in the DMEM medium, a cell density was measured, and each about 80 thousand cells were seeded on each well of a 96-well plate (Corning, CellBIND Surface).

After cultured at 37° C. for 24 hours, the medium was removed and replaced with 50 μl of a HEPES buffer, and 50 μl of a HEPES buffer containing a fluorescent calcium indicator (Fluo-4 AM attached to Molecular Devices, FLIPR Ca 4 Assay Kit) was further added. Then, this was incubated at 27° C. for 45 minutes to prepare cells to be subjected to automated fluorescent imaging.

Then, to the cells was added a HEPES buffer containing cyclamate, so that a final concentration of cyclamate became a concentration described in Table 7, and cyclamate stimulation was performed at 27° C.

Figure 21:
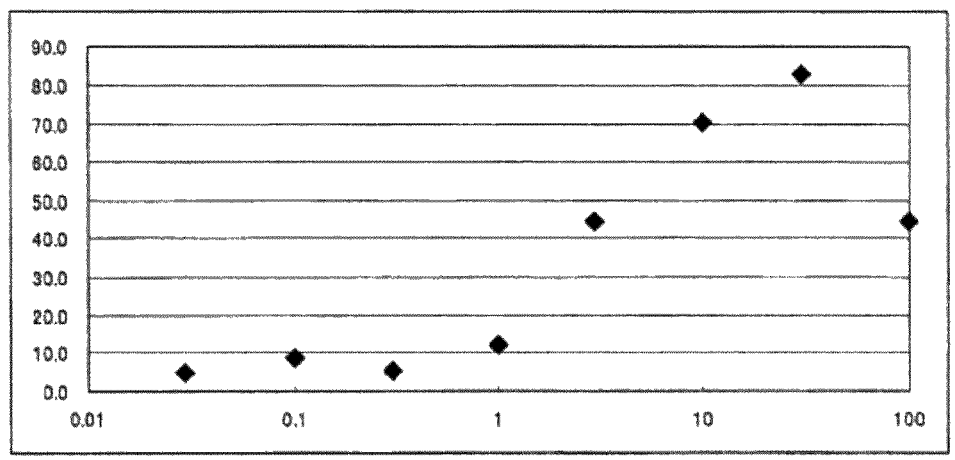
FIG. 21 shows a cyclamate concentration-response curve in case of administering cyclamate to a cultured cell strain (A).

A fluorescent reaction (excitation at 485 nm, fluorescence at 525 nm) from immediately after addition of a HEPES buffer containing cyclamate to after 100 seconds was measured by using FlexStation 3 (Molecular Devices), and a response of a sweet taste receptor-expressing cell to cyclamate stimulation was quantitated by automated fluorescent imaging. Results are shown in Table 7 and FIG. 21. The vertical axis of FIG. 21 is a maximum of change (ΔF) in a fluorescent intensity between immediately after stimulation and 100 seconds after stimulation, that is, a response intensity of cells, and the horizontal axis indicates a cyclamate concentration (mM) expressed by logarithm.

From the obtained result, it could be confirmed that a sweet taste of cyclamate can be assessed by using the cultured cell strain (A) of the present invention.

TABLE 7

| Addition concentration of cyclamate (mM) | Change amount of fluorescent intensity (ΔF) |
|---|---|
| 0.03 | 4.7 |
| 0.1 | 8.4 |
| 0.3 | 5.1 |
| 1 | 12.2 |
| 3 | 44.3 |

TABLE 7-continued

| Addition concentration of cyclamate (mM) | Change amount of fluorescent intensity (ΔF) |
|---|---|
| 10 | 70.2 |
| 30 | 83.1 |
| 100 | 44.3 |

Industrial Applicability

According to the present invention, a stable expression cell of a sweet taste receptor can be obtained. This expression cell can be utilized for analyzing a sweet taste response of a variety of substances.

We claim:

1. A sweet taste receptor-expressing construct comprising a plasmid vector comprising polynucleotides which encode
    (a) sweet taste receptor 1, member 2 (T1R2);
    (b) sweet taste receptor 1, member 3 (T1R3), and
    (c) a G protein α subunit which is hG16gust44.

2. A sweet taste receptor-expressing construct of claim 1, wherein the directional orientation of each of said polynucleotides encoding said T1R2, said T1R3, and said G protein α subunit hG16gust44 in the plasmid vector is such that the transcripts encoded thereby are also directionally oriented.

3. The sweet taste receptor-expressing construct according to claim 1, wherein the plasmid vector comprising said nucleic acid sequence is pcDNA5/FRT.

4. The sweet taste receptor-expressing construct according to claim 1, wherein the polynucleotide encoding said T1R3 is located downstream of the polynucleotide encoding said T1R2 and the polynucleotide encoding said G protein α subunit hG16gust44 is connected downstream to said T1R3 via an internal ribosome entry site (IRES) polynucleotide sequence.

5. The sweet taste receptor-expressing construct according to claim 1, which comprises a plurality of cassettes comprising
    cassette (a) comprising the polynucleotide encoding a G protein α subunit hG16gust44 which is connected immediately downstream to the polynucleotide encoding said T1R2 via an IRES sequence and cassette (b) comprising a second polynucleotide encoding G protein α subunit hG16gust44 which is connected immediately downstream to said T1R3 via an IRES sequence, wherein said cassette (b) is downstream from said cassette (a).

6. The sweet taste receptor-expressing construct according to claim 1, which comprises a plurality of cassettes comprising
    cassette (a) comprising the polynucleotide encoding said T1R2 is connected immediately downstream to the polynucleotide encoding said T1R3, via an IRES sequence and, cassette (b) comprising the polynucleotide encoding said G protein α subunit hG16gust44 which connected immediately downstream to said T1R2, via an IRES sequence, wherein said cassette (b) is downstream from said cassette (a).

7. A 293 cell strain whose genome comprises a Flippase Recognition Target (FRT) sequence and further comprising the sweet taste receptor-expressing construct according to claim 1, wherein said cell strain expresses T1R2, said T1R3, and said G protein α subunit hG16gust44 simultaneously.

8. A method for measuring a physiological response to a sweet taste substance comprising contacting said substance with the cell strain according to claim 7 and detecting and quantitating a physiological response in said cell strain resulting from a binding of said substance to said hT1R2 and said hT1R3.

9. A method for measuring a physiological response of a sweet taste substance at a concentration of a threshold or lower of a sweet taste of the sweet taste substance alone, comprising contacting a cell strain of claim 7 with a sweet taste enhancing substance for a particular sweet taste substance, wherein the sweet taste enhancing substance is identified by measuring of an enhanced physiological response to a sweet taste substance, upon measurement of a physiological response of said cells strain to the sweet taste substance in the presence of the sweet taste enhancing substance.

10. The method according to claim 8, wherein the physiological response is a change in intracellular calcium concentration.

11. The method according to claim 9, wherein the physiological response is a change in intracellular calcium concentration.

12. A sweet taste receptor-expressing construct comprising a plasmid vector comprising an internal ribosome entry site (IRES) polynucleotide sequence and polynucleotides which encode
    (a) sweet taste receptor 1, member 2 (T1R2);
    (b) sweet taste receptor 1, member 3 (T1R3), and
    (c) a G protein α subunit which is hG16gust44,
    wherein the IRES sequence links two or more of the polynucleotides of (a) to (c) and wherein directional orientation of said nucleic acids encoding said T1R2, said T1R3, and said G protein αsubunit hG16gust44 is such that the transcripts encoded thereby are also directionally oriented.

13. A sweet taste receptor-expressing construct which is
    (a) construct (a) which comprises a first cDNA encoding human sweet taste receptor 1, member 2 (hT1R2) and a second cDNA encoding human G protein α subunit which is hG16gust44 (hG16gust44), wherein the first and the second cDNAs flank an internal ribosome entry site (IRES) polynucleotide sequence and are located downstream to an EF-1α promoter, or
    (b) construct (b) which comprises a first cDNA encoding human sweet taste receptor 1, member 3 (hT1R3) and a second cDNA encoding human G protein α subunit hG16gust44 (hG16gust44), wherein the first and the second cDNAs flank an internal ribosome entry site (IRES) polynucleotide sequence and are located downstream to a CMV promoter.

14. A sweet taste receptor-expressing construct comprising a first cassette comprising a first cDNA encoding human sweet taste receptor 1, member 2 (hT1R2) located downstream to of an EF-1α promoter, and
    a second cassette comprising a second cDNA encoding human sweet taste receptor 1, member 3 (hT1R3) and a third cDNA encoding human G protein α subunit hG16gust44 (hG16gust44), wherein said second and said third cDNA, are connected downstream to a CMV promoter, wherein said CMV promoter is located downstream to the first cassette and an internal ribosome entry site (IRES) sequence is flanked by the cDNAs.

15. A sweet taste receptor-expressing construct comprising a first cDNA encoding human sweet taste receptor 1, member 3 (hT1R3) and a second cDNA encoding human sweet taste receptor 1, member 2 (hT1R2), wherein the first and the second cDNAs flank an internal ribosome entry site (IRES) polynucleotide sequence and are located downstream to a CMV promoter, and further comprising a third cDNA encoding human G protein α subunit hG16gust44 (hG16gust44), which is connected to said second cDNA encoding hT1R2, wherein the third and the second cDNAs flank a second internal ribosome entry site (IRES) polynucleotide sequence.

16. A sweet taste receptor-expressing construct prepared by
   (a) substituting 6 bases of a plasmid DNA vector pcDNA5/FRT at sites other than a multicloning site of said vector with a recognition sequence of EcoRV,
   (b) introducing a polynucleotide encoding human sweet taste receptor 1, member 3 (hT1R3) into a multicloning site of a vector obtained in the step (a),
   (c) connecting an internal ribosome entry site (IRES) polynucleotide sequence derived from pIRES2-EGFP and a polynucleotide encoding human G protein α subunit hG16gust44 (hG16gust44),
   (d) cutting a site present immediately downstream to the polynucleotide encoding T1R3 of the vector obtained in the step (b) with Not I, and inserting into said site the polynucleotide product of step (c) to yield a first construct,
   (e) inserting a polynucleotide encoding human sweet taste receptor 1, member 2 (hT1R2) into pEAK10,
   (f) cutting a site present immediately after the polynucleotide encoding T1R2 of the vector obtained in the step (e) with Not I, and inserting into said site the polynucleotide product of step (c) to yield a second construct, and
   (g) cutting the vector obtained from step (d) with EcoRV, and inserting a second construct comprising polynucleotides which respectively encode T1R2, IRES, and hG16gust44, as obtained via step (f), upstream of a first construct comprising polynucleotides which respectively encode T1R3, IRES, and hG16gust44, as obtained in step (d);
   wherein steps (b), (d) and (e) are performed independently and in any order.

17. A cell strain comprising an FRT (Flippase Recognition Target) site, wherein said FRT has been incorporated into one place in the genomic DNA of said cell, wherein said cell strain further comprises an expression construct comprising cDNAs encoding a first human sweet-taste receptor hT1R2 and a second human sweet-taste receptor hT1R3, and a G protein α subunit hG16gust44, wherein said cell (a) stably expresses said hT1R2, said hT1R3, and said G protein α subunit hG16gust44; and (b) generates a physiological response which is a change in calcium concentration via a binding of a ligand to said hT1R2 and said hT1R3.

* * * * *

SEQUENCE LISTING

```
<160> NUMBER OF SEQ ID NOS: 30

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tatagatctg atatcccccct atggtgcact ctc                                    33

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tagaaggcac agtcgagg                                                      18

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatcggcgcg ccgccatgct gggccctgct gtc                                     33

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tagaaggcac agtcgagg                                                      18

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 5
gatccggccg gcccctctcc ctcccccc                                            28

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggttgtggcc atattatc                                                       18

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatcgcggcc gcatggcccg ctcgctgacc                                          30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatcgcggcc gcgaattcac tagtgattta                                          30

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggcccgct cgctgacc                                                       18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggatgcag gctactcta                                                      19

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 11
gatcggcgcg ccgccatggg gcccagggca aag                                33

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gatcgcggcc gcctagtccc tcctcatggt                                    30

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcgggagat ctgatgcata actagtgagg ctc                                33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaccatagg gggatagcgg atccagacat gat                                33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atcgggagat ctgatgcata actagtgagg ctc                                33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaccatagg gggatagcgg atccagacat gat                                33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```
gatcggcgcg ccgccatgct gggccctgct gtc                33

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatcgcggcc gctcactcat gtttcccctg                    30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gatccggccg gccctctcc ctcccccc                       28

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggttgtggcc atattatc                                 18

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gatcggcgcg ccgccatggg gcccagggca aag                33

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gatcgcggcc gcctagtccc tcctcatggt                    30

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atggggccca gggcaaag                                 18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctggatgcag gctactcta                                          19

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatccggccg gcccctctcc ctcccccc                                28

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggttgtggcc atattatc                                           18

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatcgcggcc gcatggcccg ctcgctgacc                              30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gatcgcggcc gcgaattcac tagtgattta                              30

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atggcccgct cgctgacc                                           18

<210> SEQ ID NO 30

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctggatgcag gctactcta                                                19
```